(12) United States Patent
Haas et al.

(10) Patent No.: US 7,098,037 B2
(45) Date of Patent: Aug. 29, 2006

(54) ACCOMMODATING SUBJECT AND INSTRUMENT VARIATIONS IN SPECTROSCOPIC DETERMINATIONS

(75) Inventors: Michael J. Haas, Albuquerque, NM (US); Robert K. Rowe, Corrales, NM (US); Edward V. Thomas, Albuquerque, NM (US)

(73) Assignee: InLight Solutions, Inc., Albuquerque, NM (US)

( * ) Notice: Subject to any disclaimer, the term of this patent is extended or adjusted under 35 U.S.C. 154(b) by 456 days.

(21) Appl. No.: 10/222,721

(22) Filed: Aug. 16, 2002

(65) Prior Publication Data

US 2004/0033618 A1 Feb. 19, 2004

Related U.S. Application Data

(63) Continuation-in-part of application No. 09/672,326, filed on Sep. 28, 2000, now Pat. No. 6,528,809, which is a continuation-in-part of application No. 09/170,022, filed on Oct. 13, 1998, now abandoned, and a continuation-in-part of application No. 09/563,865, filed on May 3, 2000, now Pat. No. 6,441,388, which is a continuation-in-part of application No. 09/415,432, filed on Oct. 8, 1999, now Pat. No. 6,157,041.

(51) Int. Cl.
*G01N 33/00* (2006.01)
(52) U.S. Cl. .......................... 436/95; 436/63; 436/164; 436/166; 436/167; 436/171
(58) Field of Classification Search .............. None
See application file for complete search history.

(56) References Cited

U.S. PATENT DOCUMENTS

| 3,508,830 | A | 4/1970 | Hopkins et al. ............ 356/103 |
|---|---|---|---|
| 3,769,974 | A | 11/1973 | Smart et al. ............ 128/2.05 P |
| 4,169,807 | A | 10/1979 | Zuber ......................... 252/171 |
| 4,427,889 | A | 1/1984 | Muller ....................... 250/339 |
| 4,653,880 | A | 3/1987 | Sting et al. ................ 350/620 |
| 4,655,225 | A | 4/1987 | Dahne et al. ............... 128/633 |
| 4,661,706 | A | 4/1987 | Messerschmidt et al. ... 250/341 |
| 4,712,912 | A | 12/1987 | Messerschmidt ............. 356/73 |
| 4,730,882 | A | 3/1988 | Messerschmidt ........... 350/96.1 |
| 4,852,955 | A | 8/1989 | Doyle et al. ................ 350/1.2 |
| 4,853,542 | A | 8/1989 | Milosevic et al. .......... 250/353 |

(Continued)

FOREIGN PATENT DOCUMENTS

EP 0 280 418 A1 8/1988

(Continued)

OTHER PUBLICATIONS

Anderson, C. E. et al., "Fundamentals of calibration Transfer Through Procrustes Analysis," *Appln. Spectros.*, vol. 53, No. 10 (1999) p. 1268.

(Continued)

*Primary Examiner*—Yelena G. Gakh
(74) *Attorney, Agent, or Firm*—V. Gerald Grafe; General Counsel InLight Solutions, Inc.

(57) ABSTRACT

A method and apparatus for measuring a biological attribute, such as the concentration of an analyte, particularly a blood analyte in tissue such as glucose. The method utilizes spectrographic techniques in conjunction with an improved instrument-tailored or subject-tailored calibration model. In a calibration phase, calibration model data is modified to reduce or eliminate instrument-specific attributes, resulting in a calibration data set modeling intra-instrument or intra-subject variation. In a prediction phase, the prediction process is tailored for each target instrument separately using a minimal number of spectral measurements from each instrument or subject.

24 Claims, 14 Drawing Sheets

Spectrum of Generic Model Coefficients

U.S. PATENT DOCUMENTS

| | | | |
|---|---|---|---|
| 4,859,064 A | 8/1989 | Messerschmidt et al. ... | 356/446 |
| 4,866,644 A | 9/1989 | Shenk et al. ........... | 364/571.02 |
| 4,882,492 A | 11/1989 | Schlager ..................... | 250/346 |
| 4,975,581 A | 12/1990 | Robinson et al. ........... | 250/339 |
| 5,015,100 A | 5/1991 | Doyle ........................ | 356/445 |
| 5,019,715 A | 5/1991 | Sting et al. ................. | 250/571 |
| 5,028,787 A | 7/1991 | Rosenthal et al. .......... | 250/341 |
| 5,051,602 A | 9/1991 | Sting et al. ................. | 250/571 |
| 5,068,536 A | 11/1991 | Rosenthal ................... | 250/341 |
| 5,070,874 A | 12/1991 | Barnes et al. ............... | 128/633 |
| 5,158,082 A | 10/1992 | Jones ......................... | 128/633 |
| 5,179,951 A | 1/1993 | Knudson .................... | 128/633 |
| 5,204,532 A | 4/1993 | Rosenthal ................... | 250/341 |
| 5,222,496 A | 6/1993 | Clarke et al. ............... | 128/633 |
| 5,224,478 A | 7/1993 | Sakai et al. ................. | 128/633 |
| 5,225,678 A | 7/1993 | Messerschmidt ............ | 250/339 |
| 5,230,702 A | 7/1993 | Lindsay et al. ................ | 604/4 |
| 5,237,178 A | 8/1993 | Rosenthal et al. .......... | 250/341 |
| 5,243,546 A | 9/1993 | Maggard ............... | 364/571.02 |
| 5,299,570 A | 4/1994 | Hatschek .................... | 128/633 |
| 5,311,021 A | 5/1994 | Messerschmidt ....... | 250/339.01 |
| 5,321,265 A | 6/1994 | Block ......................... | 250/343 |
| 5,331,958 A | 7/1994 | Oppenheimer .............. | 128/633 |
| 5,348,003 A | 9/1994 | Caro .......................... | 128/633 |
| 5,351,686 A | 10/1994 | Steuer et al. ............... | 128/633 |
| 5,355,880 A | 10/1994 | Thomas et al. ............. | 128/633 |
| 5,366,903 A | 11/1994 | Lundsgaard et al. ........ | 436/165 |
| 5,372,135 A | 12/1994 | Mendelson et al. ......... | 128/633 |
| 5,379,764 A | 1/1995 | Barnes et al. ............... | 128/633 |
| 5,402,778 A | 4/1995 | Chance ....................... | 128/633 |
| 5,405,315 A | 4/1995 | Khuri et al. .................... | 604/4 |
| 5,435,309 A | 7/1995 | Thomas et al. ............. | 128/633 |
| 5,452,723 A | 9/1995 | Wu et al. .................... | 128/664 |
| 5,459,317 A | 10/1995 | Small et al. ............ | 250/341.1 |
| 5,459,677 A | 10/1995 | Kowalski et al. ...... | 364/571.02 |
| 5,490,506 A | 2/1996 | Takatani et al. ............ | 128/633 |
| 5,494,032 A | 2/1996 | Robinson et al. ........... | 128/633 |
| 5,505,726 A | 4/1996 | Meserol ......................... | 606/9 |
| 5,507,723 A | 4/1996 | Keshaviah ..................... | 604/5 |
| 5,518,623 A | 5/1996 | Keshaviah et al. ......... | 210/646 |
| 5,533,509 A | 7/1996 | Koashi et al. .............. | 128/633 |
| 5,552,997 A | 9/1996 | Massart ................. | 364/571.01 |
| 5,595,903 A | 1/1997 | Soreq et al. | |
| 5,596,992 A | 1/1997 | Haaland et al. ............. | 128/664 |
| 5,630,413 A | 5/1997 | Thomas et al. ............. | 128/633 |
| 5,636,633 A | 6/1997 | Messerschmidt et al. ... | 128/633 |
| 5,655,530 A | 8/1997 | Messerschmidt ............ | 128/633 |
| 5,681,273 A | 10/1997 | Brown .......................... | 604/6 |
| 5,708,593 A | 1/1998 | Saby et al. ............ | 364/571.04 |
| 5,724,268 A | 3/1998 | Sodickson et al. ..... | 364/571.02 |
| 5,792,050 A | 8/1998 | Alam et al. ................. | 600/310 |
| 5,823,951 A | 10/1998 | Messerschmidt ............ | 600/322 |
| 5,830,132 A | 11/1998 | Robinson .................... | 600/310 |
| 5,857,462 A | 1/1999 | Thomas et al. ............. | 128/633 |
| 5,933,792 A | 8/1999 | Andersen et al. ............. | 702/32 |
| 5,935,062 A | 8/1999 | Messerschmidt et al. ... | 600/322 |
| 6,152,876 A | 11/2000 | Robinson et al. ........... | 600/322 |
| 6,157,041 A | 12/2000 | Thomas et al. ............. | 250/573 |

FOREIGN PATENT DOCUMENTS

| | | |
|---|---|---|
| WO | WO 92/17765 | 10/1992 |
| WO | WO 93/07801 | 4/1993 |
| WO | WO 96/32631 | 10/1996 |
| WO | WO 02/065090 | 8/2002 |

OTHER PUBLICATIONS

Bantle, John P. et al., "Glucose Measurement in Patients with Diabetes Mellitus with Dermal Interstitial Fluid," Copyright ® 1997 by Mosby-Year Book, Inc., 9 pages.

Blank, T.B. et al., "Transfer of Near-Infrared Multivariate Calibrations Without Standards," *Anal. Chem.*, vol. 68 (1996) p. 2987.

Bleyer et al., "The costs of Hospitalizations Due to Hemodialysis Access Management", *Nephrology News & Issues*, Jan. 1995, pp. 19-47.

Berkoben et al., "Vascular Access for Hemodialysis", *Clnical Dialysis,* published on or before Oct. 30, 1997, 20 pages.

Daugirdas et al. "Comparison of Methods to Predict the Equilibrated Kt/V (eKt/V) in the Hemo Study", National Institutes of Health, NIDDK, Bethesda, MD, Aug. 20, 1996.

Depner et al. "Clinical Measurement of Blood Flow in Hemodialysis Access Fistulae and Grafts by Ultrasound Dilution", from the Department of Nephrology, University of California, published on or before Oct. 30, 1997, 4 pages.

Haaland, David M. et al. "Reagentless Near-Infrared Determination of Glucose in Whole Blood Using Multivariate Calibration," *Applied Spectroscopy*, vol. 46, No. 10 (1992) pp. 1575-1578.

Hakim et al., "Effects of Dose of Dialysis on Morbidity and Mortality", *American Journal of Kidney Diseases*, vol. 23, No. 5, May 1994, pp. 661-669.

Heise, H.M. "Non-Invasive Monitoring of Metabolites Using Near Infrared Spectroscopy: State of the Art," *Horm. Metab. Res.*, vol. 28 (1996) pp. 527-534.

Heise, H.M. et al., "Noninvasive Blood Glucose Sensors Based on Near-Infrared Spectroscopy," *Artif Organs*, vol. 18, No. 6 (1994) pp. 1-9.

Jacobs et al., "A Disposable urea Sensor for Continuous Monitoring of Hemodialysis Efficiency", *ASAIO Journal*, 1993, pp. M353-M358.

Jagemann, Kay-Uwe et al. "Application of Near-Infrared Spectroscopy for Non-Invasive Determination of Blood/Tissue Glucose Using Neural Networks," *Zeitschrift for Physikalische Chemie*, Bd.191, S. 179-190 (1995).

Khalil, Omar S., "Spectroscopic and Clinical Aspects of Noninvasive Glucose Measurements," Internet Article *Clinical Chemistry*, 1999; 45:165-177) 24 pages.

Keshaviah et al., "On-line monitoring of the delivery of the hemodialysis prescription", *Pediatric Nephrology*, vol. 6, 1995, pp. S2-S8.

Korte, E.H. et al., "Infrared Diffuse Reflectance Accessory for Local Analysis on Bulky Samples," *Applied Spectroscopy*, vol. 42, No. 1, Jan. 1988, pp. 38-43.

Krivitski, "Theory and Validation of Access Flow Measurement by Dilution Technique During Hemodialysis", *Kidney International*, vol. 48, 1995, pp. 244-250.

Lorber, Avraham et al., "Local Centering in Multivariate Calibration," *Journal of Chemometrics*, vol. 10 (1996) pp. 215-220.

Malin, Stephen F., "Non-Invasive Measurement of Glucose by Near Infrared Diffuse Reflectance Spectroscopy," *31st Annual Oak Ridge Conference*, Sigma Diagnostics, Inc., Apr. 23, 1999.

Marbach, "Measurement Techniques for IR Spectroscopic Blood Glucose Determination", 1993.

Marbach, R. et al. "Noninvasive Blood Glucose Assay by Near-Infrared Diffuse Reflectance Spectroscopy of the Human Inner Lip," *Applied Spectroscopy*, vol. 47, No. 7 (1993) pp. 875-881.

Marbach, R. et al. "Optical Diffuse Reflectance Accessory for Measurement of Skin Tissue by Near-Infrared Spectroscopy," *Applied Optics*, vol. 34, No. 4, Feb. 1, 1995, pp. 610-621.

McIntosh, Bruce C. et al. Quantitative Reflectance Spectroscopy in the Mid-IR, *16th Annual FACSS Conference*, Oct. 1989.

Osborne, B.G. et al., "Optical Matching of Near-Infrared Reflectance Monochromator Instruments for the Analysis of Ground and Whole Wheat," *J. Near Infrared Spectrosc.*, vol. 7 (1999) p. 167.

Ozdemir, D. et al. "Hybrid Calibration Models: An Alternative to Calibration Transfer," *Appl. Spectros.*, vol. 52, No. 4 (1998) p. 599.

Robinson, M. Ries et al., "Noninvasive Glucose Monitoring in Diabetic Patients: A Preliminary Evaluation," *Clinical Chemistry*, vol. 38, No. 9 (1992) pp. 1618-1622.

Ronco et al., "On-line urea monitoring: a further step towards adequate dialysis prescription and delivery", *Int'l Journal of Artificial Organs*, vol. 18, No. 9, 1995, pp. 534-543.

Service, F. John et al., Dermal Interstitial Glucose as an Indicator of Ambient Glycemia, *Diabetes Care*, vol. 20, No. 9, Sep. 1997, 9 pages.

Sherman, "Recirculation in the Hemodialysis Access", *Principles and Practice of Dialysis*, published on or before Oct. 30, 1997, 9 pages.

Sherman, "The Measurement of Dialysis Access Recirculation", *American Journal of Kidney Diseases*, vol. 22, No. 4, Oct. 1993, pp. 616-621.

Sjoblom, J. et al., "An Evaluation of Orthogonal Signal correction Applied to Calibration Transfer of Near Infrared Spectra," *Chemom & Intell Lab. Sys.*, vol. 44, (1998) p. 229.

Steuer et al., "A New Optical Technique for Monitoring Hematocrit and Circulating Blood Volume: Its Application in Renal Dialysis", *Dialysis & Transplantation*, vol. 22, No. 5, May 1993, 5 pages.

Sum, S.T. et al., "Standardization of Fiber Optic Probes for Near-Infrared Multivariate Calibrations," *Appl. Spectros.*, vol. 52, No. 6 (1998) p. 869.

Swierenga, H. et al., "Comparison of Two Different Approaches Toward Model Transferability in NIR Spectroscopy," *Appl. Spectros.*, vol. 52, No. 1 (1998) p. 7.

Swierenga, H. et al., "Improvement of PLS Model Transferability by Robust Wavelength Selection," *Chemom & Intell Lab. Sys. Chemom & Intell Lab. Sys.*, vol. 14 (1998) p. 237.

Wang, Y-D. et al., "Calibration Transfer and Measurement Stability of Near-Infrared Spectrometers," *Appl. Spectros.*, vol. 46, No. 5 (1992) p. 764.

Wang, Y-D. et al., "Improvement of Multivariate Calibration Through Instrument Standardization," *Anal. Chem.*, vol. 64 (1992) p. 562.

Wang, Z., "Additive Background Correction in Multivariate Instrument Standardization." *Anal. Chem.*, vol. 67 (1995) p. 2379.

Ward, Kenneth J. et al., "Post-Prandial Blood Glucose Determination by Quantitative Mid-Infrared Spectroscopy," *Applied Spectroscopy*, vol. 46, No. 6 (1992) pp. 959-965.

Webb, Paul, "Temperatures of Skin, Subcutaneous Tissue, Muscle and Core in Resting Men in Cold, Comfortable and Hot Conditions," *European Journal of Applied Physiology*, vol. 64 (1992) pp. 471-476.

Brochure entitled "Determination of Delivered Therapy Through Measreuments of Effective Clearance", Fresenius USA, Dec. 1994, 1 page.

Brochure entitled "Improve the Clinical Outcome of Every Patient", In Line Diagnostics, published on or before Oct. 30, 1997, 2 page.

Standard Deviation of Spectral Variations $Y^L$ = Library of reference spectra
$G^L$ = Library of reference values $Y^L$ denotes the library of spectra
$G^L$ denotes the corresponding library of reference values Calibration Transfer, Direct Tailoring Calibration Transfer, Composite Tailoring

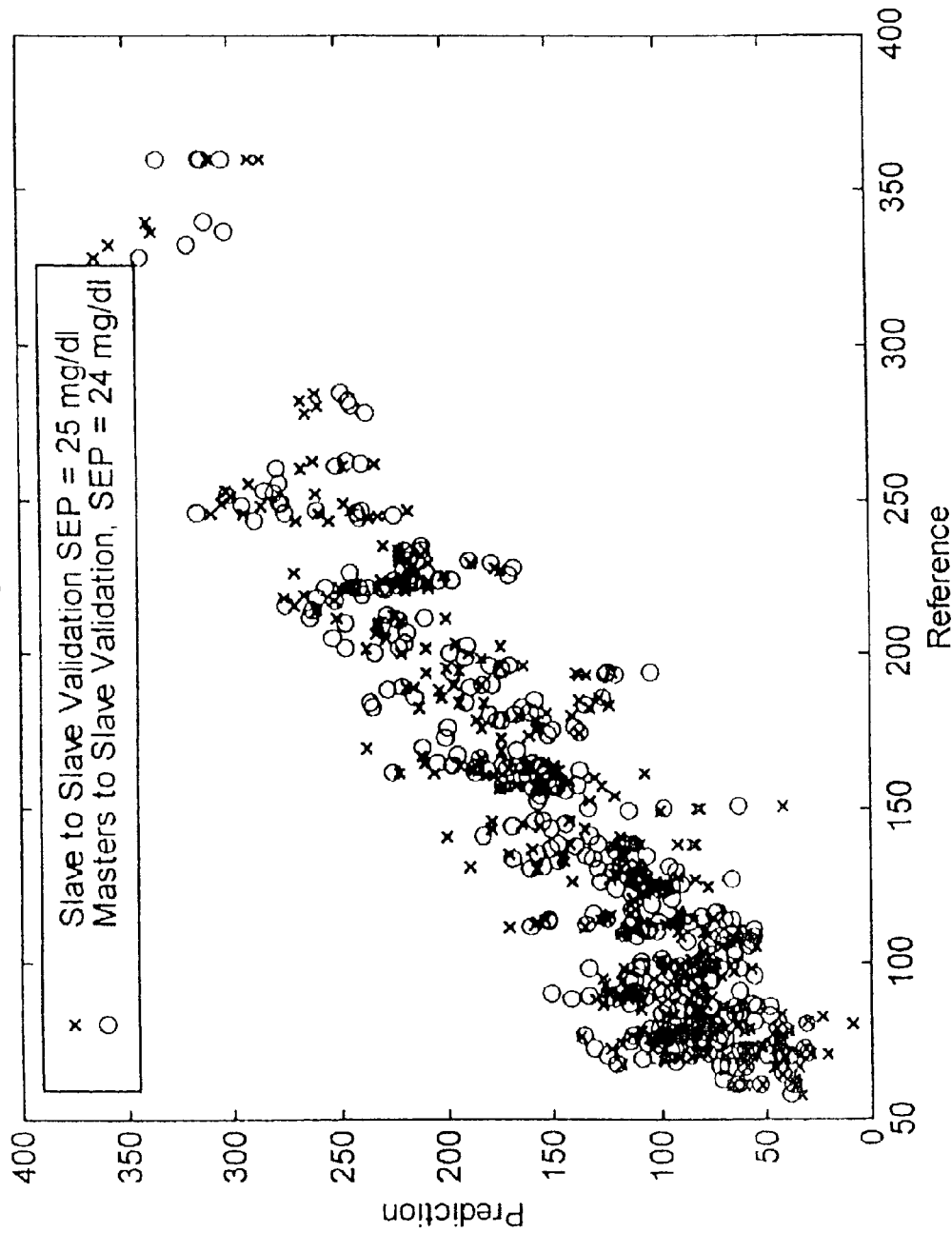

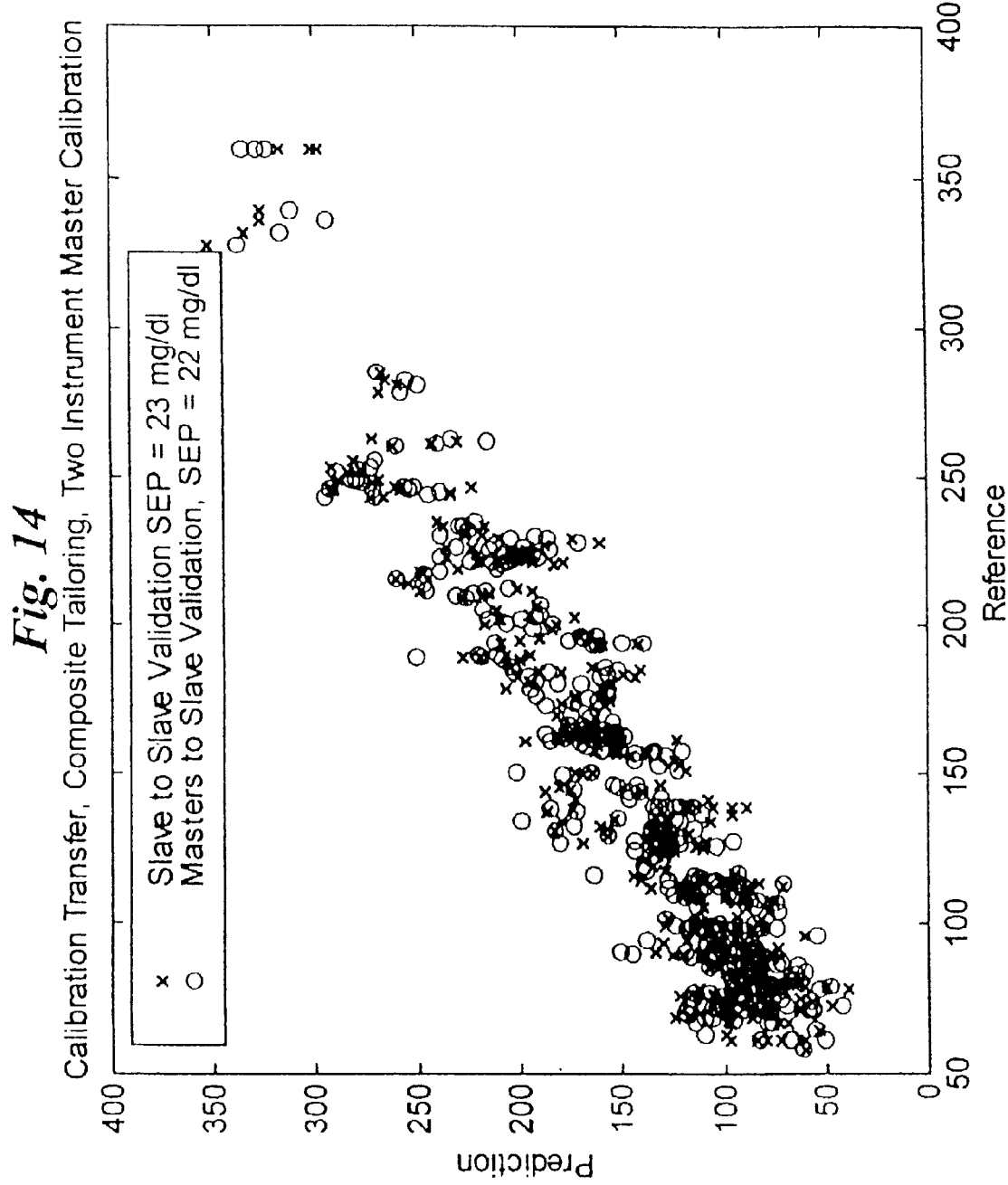

ACCOMMODATING SUBJECT AND INSTRUMENT VARIATIONS IN SPECTROSCOPIC DETERMINATIONS

CROSS REFERENCE TO RELATED APPLICATIONS

The present application claims priority as a continuation-in-part of U.S. patent application Ser. No. 09/672,326, now U.S. Pat. No. 6,528,809 B1, "Methods and Apparatus for Tailoring Calibration Models", filed Sep. 28, 2000, which is a continuation-in-part of U.S. patent application Ser. No. 09/170,022, filed Oct. 13, 1998 now abandoned; and to U.S. patent application Ser. No. 09/563,865, now U.S. Pat. No. 6,441,388 B1. "Methods and Apparatus for Spectroscopic Calibration Model Transfer", filed May 3, 2000, which is a continuation-in-part of U.S. patent application Ser. No. 09/415,432, now U.S. Pat. No. 6,157,041, filed Oct. 08, 1999, entitled "Methods and Apparatus for Tailoring Spectroscopic Calibration Models"; entitled "Multivariate Analysis Calibration Model," all of which are incorporated herein by reference.

TECHNICAL FIELD

The present invention relates generally to methods for multivariate calibration and prediction and their application to non-invasive or non-destructive measurement of selected properties utilizing spectroscopy methods. Implementations of the invention relate to multivariate calibration and prediction methods utilized in spectroscopic analysis wherein a biological sample or tissue is irradiated with infrared energy having at least several wavelengths, and differential absorption by the biological sample or tissue is measured to determine an analyte concentration or other attribute of the sample or tissue by application of the calibration model to the resulting spectral information.

BACKGROUND OF THE INVENTION

The need and demand for an accurate, non-invasive method for determining attributes of tissue, other biological samples, or analyte concentrations in tissue or blood are well documented. For example, accurate non-invasive measurement of blood glucose levels in patients, particularly diabetics, would greatly improve treatment. Barnes et al. (U.S. Pat. No. 5,379,764) disclose the necessity for diabetics to frequently monitor glucose levels in their blood. It is further recognized that the more frequent the analysis, the less likely there will be large swings in glucose levels. These large swings are associated with the symptoms and complications of the disease, whose long-term effects can include heart disease, arteriosclerosis, blindness, stroke, hypertension, kidney failure, and premature death. As described below, several systems have been proposed for the non-invasive measurement of glucose in blood. However, despite these efforts, a lancet cut into the finger is still necessary for all presently commercially available forms of home glucose monitoring. This is believed so compromising to the diabetic patient that the most effective use of any form of diabetic management is rarely achieved.

The various proposed non-invasive methods for determining blood glucose level generally utilize quantitative infrared spectroscopy as a theoretical basis for analysis. In general, these methods involve probing glucose containing tissue using infrared radiation in absorption or attenuated total reflectance mode. Infrared spectroscopy measures the electromagnetic radiation (0.7–25 μm) a substance absorbs at various wavelengths. Atoms in molecules do not maintain fixed positions with respect to each other, but vibrate back and forth about an average distance. Absorption of light at the appropriate energy causes the molecules to become excited to a higher vibration level. The excitation of the molecules to an excited state occurs only at certain discrete energy levels, which are characteristic for that particular molecule. The most primary vibrational states occur in the mid-infrared frequency region (i.e., 2.5–25 μm). However, non-invasive analyte determination in blood in this region is problematic, if not impossible, due to the absorption of the light by water. The problem is overcome through the use of shorter wavelengths of light which are not as attenuated by water. Overtones of the primary vibrational states exist at shorter wavelengths and enable quantitative determinations at these wavelengths.

It is known that glucose absorbs at multiple frequencies in both the mid- and near-infrared range. There are, however, other infrared active analytes in the tissue and blood that also absorb at similar frequencies. Due to the overlapping nature of these absorption bands, no single or specific frequency can be used for reliable non-invasive glucose measurement. Analysis of spectral data for glucose measurement thus requires evaluation of many spectral intensities over a wide spectral range to achieve the sensitivity, precision, accuracy, and reliability necessary for quantitative determination. In addition to overlapping absorption bands, measurement of glucose is further complicated by the fact that glucose is a minor component by weight in blood and tissue, and that the resulting spectral data can exhibit a non-linear response due to both the properties of the substance being examined and/or inherent non-linearities in optical instrumentation.

A further common element to non-invasive glucose measuring techniques is the necessity for an optical interface between the body portion at the point of measurement and the sensor element of the analytical instrument. Generally, the sensor element can include an input element or means for irradiating the sample point with the infrared energy. The sensor element can further include an output element or means for measuring transmitted or reflected energy at various wavelengths resulting from irradiation through the input element. The optical interface also introduces variability into the non-invasive measurement.

Robinson et al. (U.S. Pat. No. 4,975,581) disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as glucose, but also can be any chemical or physical property of the sample. The method of Robinson et al. involves a two-step process that includes both calibration and prediction steps. In the calibration step, the infrared light is coupled to calibration samples of known characteristic values so that there is differential attenuation of at least several wavelengths of the infrared radiation as a function of the various components and analytes comprising the sample with known characteristic value. The infrared light is coupled to the sample by passing the light through the sample or by reflecting the light from the sample. Absorption of the infrared light by the sample causes intensity variations of the light that are a function of the wavelength of the light. The resulting intensity variations at the at least several wavelengths are measured for the set of calibration samples of known characteristic values. Original or transformed intensity variations are then empirically related to the known characteristic of the calibration samples using a multivariate algorithm to obtain a multivariate calibration model. In the prediction step, the infrared light is coupled to a sample of unknown characteristic value, and the calibration model is applied to the original or transformed intensity variations of the appropriate wavelengths of light measured from this unknown sample. The result of the prediction step is the estimated value of the characteristic of the unknown sample. The disclosure of Robinson et al. is incorporated herein by reference.

Barnes et al. (U.S. Pat. No. 5,379,764) disclose a spectrographic method for analyzing glucose concentration wherein near infrared radiation is projected on a portion of the body, the radiation including a plurality of wavelengths, followed by sensing the resulting radiation emitted from the portion of the body as affected by the absorption of the body. The method disclosed includes pretreating the resulting data to minimize influences of offset and drift to obtain an expression of the magnitude of the sensed radiation as modified.

Dähne et al. (U.S. Pat. No. 4,655,225) disclose the employment of near infrared spectroscopy for non-invasively transmitting optical energy in the near-infrared spectrum through a finger or earlobe of a subject. Also discussed is the use of near infrared energy diffusely reflected from deep within the tissues. Responses are derived at two different wavelengths to quantify glucose in the subject. One of the wavelengths is used to determine background absorption, while the other wavelength is used to determine glucose absorption.

Caro (U.S. Pat. No. 5,348,003) discloses the use of temporally modulated electromagnetic energy at multiple wavelengths as the irradiating light energy. The derived wavelength dependence of the optical absorption per unit path length is compared with a calibration model to derive concentrations of an analyte in the medium.

Wu et al. (U.S. Pat. No. 5,452,723) disclose a method of spectrographic analysis of a tissue sample which includes measuring the diffuse reflectance spectrum, as well as a second selected spectrum, such as fluorescence, and adjusting the spectrum with the reflectance spectrum. Wu et al. assert that this procedure reduces the sample-to-sample variability.

The intended benefit of using models such as those disclosed above, including multivariate analysis as disclosed by Robinson, is that direct measurements that are important but costly, time consuming, or difficult to obtain, can be replaced by other indirect measurements that are cheaper and easier to get. However, none of the prior art modeling methods, as disclosed, has proven to be sufficiently robust or accurate to be used as a surrogate or replacement for direct measurement of an analyte such as glucose.

Of particular importance to the present invention is the use of multivariate analysis. Measurement by multivariate analysis involves a two-step process. In the first step, calibration, a model is constructed utilizing a dataset obtained by concurrently making indirect measurements and direct measurements (e.g., by invasively drawing or taking and analyzing a biological sample such as blood for glucose levels) in a number of situations spanning a variety of physiological and instrumental conditions. A general form for the relationship between direct (blood-glucose concentration) and the indirect (optical) measurements is $\hat{G}=f(y_1, y_2, \ldots, y_q)$, where $\hat{G}$ is the desired estimated value of the direct measurement (glucose), $f$ is some function (model), and $y_1, y_2, \ldots, y_q$ (the arguments of $f$) represents the indirect (optical) measurement, or transformed optical measurements, at q wavelengths. The goal of this first step is to develop a useful function, $f$. In the second step, prediction, this function is evaluated at a measured set of indirect (optical) measurements $\{y_1, y_2, \ldots, y_q\}$ in order to obtain an estimate of the direct measurement (blood-glucose concentration) at some time in the future when optical measurements will be made without a corresponding direct or invasive measurement.

Ideally, one would prefer to develop a calibration model that is applicable across all subjects and all instruments (i.e., instruments used to make the measurements). The ability to use a calibration developed on one instrument on another instrument is referred to as calibration transfer. The instrument or instruments that are used for collection of the calibration data are referred to as master instruments. Master instruments can be completely different instruments or an instrument(s) that are modified to produce different instrument conditions or states. The master instruments are used to produce calibration data which is typically composed of spectra and direct reference values. The calibration data can be used in raw form or processed in multiple ways to create calibration information. Calibration information can be simply the raw data, a calibration model, an eigenvector decomposition of the data, or any other suitable representation of the information content contained in the master calibration data. The calibration information is then used by a slave instrument such that the slave instrument can make prediction measurements. A slave instrument is simply an instrument that uses the master calibration information. In practice, the slave instrument is a production version of the master instruments. The slave instrument is manufactured to be the same as the master instrument, but variances in manufacturing result in measurable differences. The development of a single calibration model that works across these manufacturing differences is referred to as a universal model. A universal model or calibration is a calibration that can be transferred from the master instrument or instruments to the slave without adaptation, correction or other modifications. Universal models have been referred to as global calibration models in the literature. However, it has been shown that for many applications, subject and instrument variability make it difficult to develop a universal calibration model. Subject and instrument variability are specifically addressed in U.S. patent application Ser. No. 09/415,432, which has been incorporated by reference. The magnitude and general complexity of variation can be characterized by the standard deviation of the spectral data. FIG. 1 graphically illustrates the difference between inter-instrument variation and intra-instrument variation. The spectral data used to generate the figure was acquired over a six-week period and utilized 175 background measurements made on three different instruments. The inter-instrument variation is the standard deviation of the spectral data acquired over the time period. The intra-instrument variation was calculated by first meancentering the spectral data by instrument with subsequent calculation of the standard deviation. The spectral variation across instruments, inter-instrument spectral variation, is substantially larger than the intra-instrument variation and has a more complex spectral shape. The inter-instrument variation includes all spectral differences between the instruments, as well as the intra-instrument variations observed over the data acquisition period. Sources of spectral variation within an instrument include alignment changes, environmental changes, etc. The spectral variation across instruments is substantially larger than the sum of all effects within an instrument. Thus, the task of building a universal calibration model that will be effective across instruments is a daunting one.

Various attempts have been made to address instrument variability, but with limited success. For example, U.S. Pat. No. 4,866,644 to Shenk et al. teaches a method of developing an explicit correction for the spectra generated by each field instrument based upon the measurement of a common set of standard samples measured on the master and field instruments. U.S. Pat. No. 5,243,546 to Maggard teaches a method of developing an explicit correction to the calibration model for each field instrument based upon the measurement of a common set of standard samples measured on the master and field instruments. U.S. Pat. No. 5,459,677 to Kowalski et al. teaches a method of developing an explicit correction ("transfer coefficients") for the spectra generated by each field ("target") instrument based upon the measurement of a common set of standard samples measured on the master ("reference") and field instruments. U.S. Pat. No. 5,552,997 to Massart teaches a method of developing and validating an explicit univariate calibration for each analytical instrument based upon the measurement of a set of standard samples with known reference values measured on the instrument of interest, allowing for changes in bias, slope and curvature. However, Massart does not address transfer of calibration, nor does Massart address a multivariate framework. U.S. Pat. No. 5,724,268 to Sodickson et al. teaches a method of estimating and compensating for spectral errors introduced by spectroscopic instrumentation by estimating and accounting for the error sources using least-squares or other mathematical estimation techniques.

A number of methods have also been proposed in the literature for transferring a calibration from one near-infrared spectrometer based instrument to another. These methods can be classified into four general categories: (1) pre-processing, (2) hybrid models, (3) wavelength selection, and (4) transformations. Methods within each category can be generally effective at compensating for certain instrument-to-instrument differences.

A pre-processing method is described in C. E. Anderson, J. H. Kalivas, "Fundamentals of Calibration Transfer Through Procrustes Analysis", *Appl. Spectros.*, 53(10), 1268 (1999). This method employs a statistical methodology called Procrustes analysis and, in particular, highlights a process they call translation. The authors conclude that "translation is the key step for transformation of spectra and can often be all that is required" to achieve calibration transfer. This technique can require a common set of samples to be measured on both the master and slave instruments.

Another pre-processing method called "orthogonal signal correction" is described by J. Sjoblom et al. in "An Evaluation of Orthogonal Signal Correction Applied to Calibration Transfer of Near Infrared Spectra", *Chemom & Intell Lab. Sys.*, 44, 229 (1998). This method can require a common set of samples to be measured on both the master and slave instruments and is reported to perform at about the same level as other known calibration transfer methods (piece-wise direct standardization and hybrid modeling).

Another pre-processing method wherein the derivative spectra are used for calibration and validation is compared to piece-wise direct standardization (PDS) in H. Swierenga et al., "Comparison of Two Different Approaches Toward Model Transferability in NIR Spectroscopy", *Appl. Spectros.*, 52(1), 7 (1998). It was reported that, in some cases, using derivative spectra was as effective as PDS, but in other cases, it performed poorly compared to PDS.

Hybrid modeling, wherein samples measured on both instruments are used directly in building the calibration, has been applied to a calibration transfer problem as described in D. Ozdemir et al., "Hybrid Calibration Models: An Alternative to Calibration Transfer", *Appl. Spectros.*, 52(4), 599 (1998). Results reportedly show that when using a multivariate analysis method such as partial least squares (PLS) to build a calibration, effective models should be constructed, but equal number of samples should be measured on both the master and slave instruments.

Wavelength selection, a method which attempts to identify and use only those wavelengths that contain information pertinent to the analyte of interest and minimize the inclusion of wavelengths that contain only instrument-specific data, has been applied to problems in calibration transfer. It has been reported by H. Swierenga et al. in "Improvement of PLS Model Transferability by Robust Wavelength Selection", *Chemom. Intell. Lab. Syst.*, 14, 237 (1998) that wavelength selection can perform calibration transfers as effectively as PDS.

Direct standardization and piece-wise direct standardization are methods used for calibration transfer that rely on the measurement of a number of standard samples on both the master and slave instruments. These methods are described by Y -D. Wang and B. R. Kowalski in "Calibration Transfer and Measurement Stability of Near-Infrared Spectrometers", *Appl. Spectros.*, 46(5), 764 (1992) and others (see, e.g., Y - D. Wang, M. J. Lysaght, B. R. Kowalski, "Improvement of Multivariate Calibration Through Instrument Standardization", *Anal. Chem.*, 64, 562 (1992); and Z. Wang, "Additive Background Correction in Multivariate Instrument Standardization", *Anal. Chem.*, 67, 2379 (1995)).

A technique called "optical matching" is reported by B. G. Osborne et al. in "Optical Matching of Near Infrared Reflectance Monochromator Instruments for the Analysis of Ground and Whole Wheat", *J. Near Infrared Spectrosc.*, 7, 167 (1999). This method again can require the use of a set of transfer samples measured on both instruments.

Techniques employing finite impulse response filters have been described by S. T. Sum and S. D. Brown in "Standardization of Fiber Optic Probes for Near-Infrared Multivariate Calibrations", *Appl. Spectros.*, 52(6), 869 (1998) and by T. B. Blanket al. in "Transfer of Near-infrared Multivariate Calibrations Without Standards", *Anal. Chem.*, 68, 2987 (1996). Although FIR filtering methods were generally found to be successful, this method was not as effective as PDS when a bias was present between the master and slave instruments.

In addition, it should be noted that efforts have been made to create calibration models that are robust to various instrumental changes that can occur after the calibration period. In "Strategy for Constructing Robust Multivariate Calibration Models", *Chemometrics and Intelligent Laboratory Systems*, 49, 1–17 (1999), Swierenga et al. describe methods of assessing a calibration's sensitivity to environmental effects and apply various pre-processing techniques on the calibration set in order to reduce this sensitivity.

A method of selecting "robust variables", resulting in a more robust calibration, is described by Swierenga et al. in "Development of Robust Calibration Models in Near Infra-Red Spectrometric Applications", *Anal. Chim. Acta*, 411, 121–135 (2000). This work compares the effectiveness of selecting "robust variables" with the method of including the external variations in the calibration set.

Ozdemir et al. report in "Effect of Wavelength Drift on Single and Multi-instrument Calibration Using Genetic Regression", *Applied Spectroscopy*, 52, 1203–1209 (1998)

that, in simulation, inclusion of wavelength shifted spectra in the calibration serves to make the model more robust to wavelength shifts in the spectra of the validation set.

Near-infrared spectroscopy has been applied to many quantitative and qualitative analysis problems encountered in both academia and industry. Various techniques for creating a useful calibration model for a particular instrument have been proposed as discussed previously (for example, see *Multivariate Calibration,* H. Martens and T. Naes, 1989, Wiley and Sons Ltd.), but effective techniques for maintaining this calibration model on the same instrument across changes to the environment or instrument, or transferring the calibration model to another instrument have not been universally accepted.

The need for applying a single calibration model to multiple instruments arises in a variety of fields including, but not limited to, process and quality control. Applying a calibration model from one instrument to data collected on another (slave) instrument is made difficult by differences in instruments that give rise to a number of spectral effects (for example, instrument response, resolution, photometric accuracy, etc.). These differences will tend to introduce elevated errors in the predictions made by the slave instrument. These additional prediction errors can, in general, be classified as due to some combination of bias, slope, and precision. Bias errors are those that represent a fixed error, common to all predictions made on the slave instrument. Slope errors are those that are proportional to the magnitude of the attribute of biological tissue being measured, such as glucose concentration. Precision errors are calculated as the additional prediction error that is not ascribable to bias or slope.

In general, the process of creating a calibration model for a particular instrument is time consuming and expensive, and therefore impractical for applications requiring the use of multiple instruments or using a single instrument in different environments or with different sampling accessories. A method for transferring a calibration from one (master) instrument to another (slave) instrument (or multiple slave instruments) with minimal effort would be beneficial in a wide variety of fields employing near infrared spectroscopy.

Accordingly, the need exists for a method and apparatus for non-invasively measuring attributes of biological tissue, such as glucose concentrations in blood, which incorporates a model that is sufficiently robust to act as an accurate surrogate for direct measurement. The model would preferably account for instrument and subject variability. Specifically, the methods and apparatus should provide a model that eliminates or significantly reduces all forms of excess prediction error manifested as bias, slope or precision errors. In order to be commercially successful, applicants believe, the model should not require extensive sampling of the specific instrument and/or subject on which the model is to be applied in order to accurately predict a biological attribute such as glucose.

The present invention addresses these needs as well as other problems associated with existing models and calibrations used in methods for non-invasively measuring an attribute of a biological sample such as glucose concentration in blood. The present invention also offers further advantages over the prior art and solves problems associated therewith.

SUMMARY OF THE INVENTION

The present invention comprises a method that reduces the level of interfering spectral variation for which a multivariate calibration model must compensate. An application of the invention is the non-invasive measurement of an attribute of a biological sample such as a tissue characteristic (e.g., glycosolation effects) or an analyte (e.g., glucose), in human tissue. The invention utilizes spectroscopic techniques in conjunction with improved protocols and methods for acquiring and processing spectral data. The invention comprises protocols and data-analytic methods that enable a clear definition of intra-instrument spectral effects while reducing inter-instrument spectral effects. The resulting data, which have reduced inter-instrument spectroscopic variation, can be utilized in a prediction method that is specific for a given instrument or tailored (or adapted) for use on the specific instrument. The prediction method uses a minimal set of reference samples from that instrument for generation of valid prediction results.

A preferred method for non-invasively measuring a tissue attribute, such as the concentration of glucose in blood, includes first providing an apparatus for measuring infrared absorption by a biological sample such as an analyte containing tissue. The apparatus can include three elements: an energy source, a sensor element, and a spectrum analyzer. The sensor element includes an input element and an output element. The input element is operatively connected to the energy source by a first means for transmitting infrared energy. The output element is operatively connected to the spectrum analyzer by a second means for transmitting infrared energy.

In practicing a preferred method of the present invention, an analyte-containing tissue area is selected as the point of analysis. This area can include the skin surface on the finger, earlobe, forearm, or other skin surface. A preferred sample location is the underside of the forearm. The sensor element, which includes the input element and the output element, is placed in contact with the skin. In this way, the input element and output element are optically coupled to the analyte containing tissue or skin surface In analyzing for a biological attribute, such as the concentration of glucose in the analyte containing tissue, light energy from the energy source is transmitted via a first means for transmitting infrared energy into the input element. The light energy is transmitted from the input element to the skin surface. Some of the light energy contacting the analyte-containing sample is differentially absorbed and scattered by the various components and analytes contained therein at various depths within the sample. A quantity of light energy is collected by the output element (e.g., by reflection, transmission, or a combination thereof). The non-absorbed reflected light energy is then transmitted via the second means for transmitting infrared energy to the spectrum analyzer. As detailed below, the spectrum analyzer preferably utilizes a computer and associated memory device to generate a prediction result utilizing the measured intensities and a calibration model from which a multivariate algorithm is derived.

Applicants have found that, in the case of the noninvasive prediction of glucose by spectroscopic means, application of known multivariate techniques to spectral data will not produce a predictive model that yields sufficiently accurate predictions for future use. In order to obtain useful predictions, the spectral contribution from the particular analyte or attribute of interest can be extracted from a complex and varying background of interfering signals. The interfering signals vary across and within instruments and can be broadly partitioned into "intra-instrument" and "inter-instrument" sources. Some of these interfering signals arise from fabrication differences between instruments. The net effect of the cumulative interfering signals due to inter-instrument variations is a degradation in performance when the calibration developed in one instrument (hereinafter referred to as the master instrument) is used to generate prediction results on another instrument (hereinafter referred to as the slave instrument). This degradation in performance can be reduced or minimized by building identical or clone instruments, but this strict requirement of sameness can increase production cost, if such level of sameness is even possible.

The present invention involves a prediction process that reduces the impact of instrument-specific effects on prediction through a tailoring process, while concurrently facilitating the modeling of intra-instrument effects. The tailoring process is used to adapt the model so that it predicts accurately for a given instrument. An experimental observation is that intra-instrument spectral effects are moderately consistent across instruments that are built in a similar manner. Thus, intra-instrument spectral variation observed from a set of instruments can be used to enhance or strengthen the calibration for subsequent use on an individual instrument not included in the set. This results in a prediction process that is specific for use on a given instrument, but where intra-instrument information from other instruments is used to enhance the performance of the monitoring device.

Spectroscopic data that have been acquired and processed in a manner that reduces inter-instrument spectroscopic variation while maintaining intra-instrument variation are herein referred to as generic calibration data. These generic data, which comprise a library of intra-instrument variation, are representative of the likely variation that might be observed over time for any particular instrument. In order to be effective, the intra-instrument spectral variation manifested in the generic calibration data can be representative of future intra-instrument spectral effects.

Intra-instrument effects can be caused by many influences, some of which are listed below. Changes in the illumination system due to alignment changes, environmental changes such as humidity or temperature, bulb changes, optical filter aging, optical filter changes due to temperature, changes in optical surface quality, bulb aging, and power supply fluctuations. Changes in the detector or detectors due to temperature changes of the detector, linearity changes, environmental changes, or response changes. Changes in the data acquisition system due to temperature changes of the electronics, linearity changes, environmental changes, or response changes. Changes in the instrument-sample interface to include changes in throughput, pathlength, sampling error, changes in optical surface quality or spectral response. Spectrometer changes due to environmental changes, chromatic aberration, spatial response function, angular response function, component changes due to aging, vibration, changes in optical surface quality, temperature and humidity, changes in modulation efficiency, throughput, wavelength drift, and apodization changes. The preceding list of intra-instrument sources of variation is an incomplete list of all the different types of variation that are present in optical instrumentation. It is important to note that the generic calibration data preferably include spectroscopic effects associated with the instrument utilized. Thus, it is important to use an appropriate experimental protocol to provide representation of these intra-instrument spectral effects.

In prediction embodiments of the present invention, multivariate techniques are applied to the generic calibration data to derive an instrument-specific predictor of the direct measurement. Each prediction embodiment uses the generic calibration data in some raw or altered condition in conjunction with at most a few reference spectra from a specific instrument to achieve a tailored prediction method that is an accurate predictor of a desired indirect measurement for that particular instrument. Reference spectra are spectroscopic measurements from a specific instrument that are used in the development of a tailored prediction model. Reference analyte values quantify the concentration of the analyte (via direct methods) and can be used in the development of a tailored prediction model. Applicants have developed several embodiments that incorporate the above concepts.

Each tailored prediction method described herein utilizes generic calibration data. Generic calibration data can be created by a variety of data acquisition and processing methods. In a first preferred processing method, the generic calibration data are obtained by acquiring a series of indirect measurements from one or more instruments and a direct measurement for each instrument corresponding to each indirect measurement. It is important to note that intra-instrument variation can be captured many different ways. In one case, a single instrument can be observed in many different instrument states by subjecting the instrument to conditions that results in intra-instrument variation. For example changing the bulb, changing bulb power, temperature cycling the instrument, etc., can create different intra-instrument states. In an alternative case, multiple instruments can be used to capture different intra-instrument states. An appropriate experimental protocol is needed to provide adequate representation of intra-instrument effects that are expected in the future (including those associated with the instrument of interest). The mean indirect measurement and the mean direct measurement for each instrument based on the number of measurements from that instrument are then formed. The indirect measurements are meancentered by subtracting the mean indirect measurement of each instrument from each of that instrument's indirect measurements. The direct measurements are meancentered by subtracting the mean direct measurement of each instrument from each of that instrument's direct measurements. That is, the instrument-specific mean indirect measurements and instrument-specific mean direct measurements act as instrument-specific subtrahends. The sets of meancentered measurements (indirect and direct) comprise the generic calibration data.

There are a number of other related ways for creating generic calibration data with an instrument-specific subtrahend. For example, the instrument-specific subtrahends for the indirect and direct measurements could be some linear combination of each instrument's indirect and direct measurements, respectively.

In one other specific method for creating generic calibration data, the instrument-specific subtrahends for the indirect and direct measurements consist of the mean of the first S indirect measurements of each instrument and the mean of the first S direct measurements of each instrument, respectively. Alternately, a moving window reference technique could be utilized wherein the subtrahends are the instrument-specific means of the S nearest (in time) indirect and direct measurements, where S is less than the total number of reference measurements made on a particular instrument. The value of S can be chosen to fit the constraints of the particular application, neglecting effects due to random noise and reference error.

In another alternative processing method, the generic calibration data can be produced in a round-robin reference manner wherein you subtract each instrument's reference data from every other instrument's reference measurement made on that instrument in a round-robin fashion.

In a further alternative processing method which is particularly useful when a spectral library associated with a large number of instruments exists, the generic calibration data are created by subtracting some linear combination of spectral library data in order to minimize inter-instrument spectral features. Instrument-specific attributes can be reduced by subtracting some linear combination of similar spectra. That is, the instrument-specific subtrahend for a given instrument consists of a linear combination of spectra obtained from one or more instruments, each of which are different than the given instrument. In one embodiment, the spectrum of a given instrument would be matched with a combination of similarly appearing spectra from other instruments. In another embodiment, one would match the spectrum of a given instrument with a combination of spectra from other instruments where the matching criteria involve measurable parameters such as throughput, modulation efficiency, wavelength axis, absorbance response, chromatic aberration, spectral response, spatial response functions, angular response functions, etc.

In an alternative processing method, the generic calibration data are created through simulation in a manner that minimizes instrument-specific spectral attributes. This methodology can require accurate modeling and subsequent simulation of the sample under examination, the optical system, the sampler-tissue interface, and all other contributors to spectral variation. Generic calibration data can be simulated directly or instrument data can be simulated. The simulated instrument spectra can subsequently be processed by any of the preceding five processing methods. In an additional embodiment, the simulated data can be combined with real instrument data for the creation of a combined simulated/real generic calibration data.

Once the generic calibration data have been created, such data is then utilized to create a tailored prediction process specific for a particular instrument for use in future predictions of the attribute. The tailored prediction process can be accomplished in several ways.

A direct way to tailor the prediction process to a given instrument is as follows and will be denoted as direct tailoring. First, the generic calibration data are used to develop an intra-instrument calibration model for the instrument of interest. This model herein is referred to as a generic model. By design, the generic model will produce predictions that are essentially unaffected by intra-instrument spectral variation that is represented in the generic calibration data and not associated with the instrument of interest. On the other hand, the generic model will produce predictions that are appropriately sensitive to the instrument of interest. The generic model is applied directly to at least one indirect measurement from a target instrument for which there are corresponding direct measurements. The resulting predictions of the generic model are averaged. The difference between the average of the direct measurements and average prediction is computed. This instrument-specific difference is added to the subsequent predictions of the generic model as applied directly to the future indirect measurements from the target instrument. The resultant sums comprise the net predictions of the direct measurement corresponding to the future indirect measurements from the target instrument. It is important to note that a single generic model can be used in the tailoring process for a number of target instruments.

A second tailored prediction embodiment uses a combination of at least two instrument reference spectra, reference analyte values and the generic calibration data to create a prediction model that is specific for use on the particular instrument. The technique by which the calibration data and reference spectra are combined uses a linear combination of the data in absorbance units. The combinations of calibration data and reference data can be done in a structured or random way. It is the applicants' observation that random associations work effectively and are easily implemented. The process of creating these composite data is referred to as robustification. The resulting calibration spectra contain the reference spectra from the particular instrument combined with spectral data that contain sources of spectroscopic variation associated with instrument variation such as changes due to illumination system, detector, data acquisition system, sampler, or spectrometer, variations associated with sampling techniques, and spectroscopic effects associated with the instrument of interest. The composite calibration data can be processed to develop a calibration model. The resulting model will be referred to hereafter as a composite calibration model. The resulting composite calibration model is specific for a particular instrument and can be used to generate analyte prediction results for the particular instrument. In the use of either tailored prediction process, reference spectra and reference analyte values are utilized. The reference information is used in combination with the generic calibration data to create a tailored prediction process for use on the particular instrument. In general terms, the instrument reference information is used to tailor a general processing method for use on a particular instrument. In an additional embodiment, the instrument reference spectra can be replaced by the use of an instrument-matched spectrum or a set of matched spectra. Matched spectra are spectra from another instrument or a combined spectrum that interacts with the calibration model in a manner similar to the instrument to be predicted upon. In use, a never-before-seen instrument is tested and at least one spectrum is obtained. The resulting spectrum is used for generating a prediction result and as a reference spectrum. In use and in contrast to the two prior embodiments, no reference analyte value is used or needed. The implementation of this method involves the following:

1. Identification or creation of a matched spectra through use of the reference spectra.
2. Replacement of the reference spectra with the corresponding matched spectra.
3. Although reference analyte values are not obtained from the never-before-seen instrument, matched analyte values from the corresponding matched spectra are used in the processing method in a manner consistent with the prior uses of reference analyte values.
4. Use of either tailored prediction process.

In practice, the spectral data from the never-before-seen instrument is compared with spectral data that has corresponding attribute reference values in a spectral library to identify the best or several matched spectra. Matched spectra are spectra from another instrument that appear similar when processed by the calibration model.

As stated previously, the application of known multivariate analysis techniques for calibration transfer have deficiencies due to cost, complexity, or resulting prediction performance degradation. The processing method described overcomes these known limitations by using a matched spectrum. Thus, the instrument tailoring with this method is accomplished without an actual reference analyte value from the individual instrument. The matched spectrum method in conjunction with either tailored prediction process can require a large spectral library to facilitate the appropriate matching between the instrument to be predicted upon and at least one library spectrum. In implementation of this matching method, applicants have identified matched spectra by finding those spectra that are most consistent with the calibration model as reflected by such parameters as Mahalanobis distance and spectral residual metrics. Other methods of spectral match would also have applicability for determination of matched spectra.

The invention further comprises of protocols and data-analytic methods that enable a clear definition of intra-subject spectral effects while reducing inter-subject spectral effects. The resulting data, which have reduced inter-subject spectroscopic variation, can be utilized in a prediction method that is specific for a given subject or tailored (or adapted) for use on the specific subject. The prediction method uses a minimal set of reference samples from that subject for generation of valid prediction results.

Applicants have found that, in the case of the noninvasive prediction of glucose by spectroscopic means, application of known multivariate techniques to spectral data, will not produce a predictive model that yields sufficiently accurate predictions for future use. In order to obtain useful predictions, the spectral contribution from the particular analyte or attribute of interest can be extracted from a complex and varying background of interfering signals. The interfering signals vary across and within subjects and can be broadly partitioned into "intra-subject" and "inter-subject" sources. Some of these interfering signals arise from other substances that vary in concentration. The net effect of the cumulative interfering signals is such that the application of known multivariate analysis methods does not generate prediction results with an accuracy that satisfies clinical needs.

The present invention involves a prediction process that reduces the impact of subject-specific effects on prediction through a tailoring process, while concurrently facilitating the modeling of intra-subject effects. The tailoring process is used to adapt the model so that it predicts accurately for a given subject. An experimental observation is that intra-subject spectral effects are consistent across subjects. Thus, intra-subject spectral variation observed from a set of subjects can be used to enhance or strengthen the calibration for subsequent use on an individual not included in the set. This results in a prediction process that is specific for use on a given subject, but where intra-subject information from other subjects is used to enhance the performance of the monitoring device.

Spectroscopic data that have been acquired and processed in a manner that reduces inter-subject spectroscopic variation while maintaining intra-subject variation are herein referred to as generic calibration data. These generic data, which comprise a library of intra-subject variation, are representative of the likely variation that might be observed over time for any particular subject. In order to be effective, the intra-subject spectral variation manifested in the generic calibration data can be representative of future intra-subject spectral effects such as those effects due to physiological variation, changes in the instrument status, sampling techniques, and spectroscopic effects associated with the analyte of interest. Thus, it is important to use an appropriate experimental protocol to provide representation of these intra-subject spectral effects.

In each prediction embodiment of the present invention, multivariate techniques are applied to the generic calibration data to derive a subject-specific predictor of the direct measurement. Each prediction embodiment uses the generic calibration data in some raw or altered condition in conjunction with at most a few reference spectra from a specific subject to achieve a tailored prediction method that is an accurate predictor of a desired indirect measurement for that particular subject. Reference spectra are spectroscopic measurements from a specific subject that are used in the development of a tailored prediction model. Reference analyte values quantify the concentration of the analyte (via direct methods) and can be used in the development of a tailored prediction model. Applicants have developed several embodiments that incorporate the above concepts.

Each tailored prediction method described herein utilizes generic calibration data. Generic calibration data can be created by a variety of data acquisition and processing methods. In a first preferred processing method, the generic calibration data are obtained by acquiring a series of indirect measurements from one or more subjects and a direct measurement for each subject corresponding to each indirect measurement. An appropriate experimental protocol is needed to provide adequate representation of intra-subject effects that are expected in the future (including those associated with the analyte of interest). The mean indirect measurement and the mean direct measurement for each subject based on the number of measurements from that subject are then formed. The indirect measurements are mean centered by subtracting the mean indirect measurement of each subject from each of that subject's indirect measurements. The direct measurements are mean centered by subtracting the mean direct measurement of each subject from each of that subject's direct measurements. That is, the subject-specific mean indirect measurements and subject-specific mean direct measurements act as subject-specific subtrahends. The sets of mean-centered measurements (indirect and direct) comprise the generic calibration data.

There are a number of other related ways for creating generic calibration data with a subject-specific subtrahend. For example, the subject-specific subtrahends for the indirect and direct measurements could be some linear combination of each subject's indirect and direct measurements, respectively.

In another specific method for creating generic calibration data, the subject-specific subtrahends for the indirect and direct measurements consist of the mean of the first S indirect measurements of each subject and the mean of the first S direct measurements of each subject, respectively. Alternately, a moving window reference technique could be utilized wherein the subtrahends are the subject-specific means of the S nearest (in time) indirect and direct measurements, where S is less than the total number of reference measurements made on a particular subject. The value of S can be chosen to fit the constraints of the particular application, neglecting effects due to random noise and reference error.

In another alternative processing method, the generic calibration data can be produced in a round-robin reference manner wherein you subtract each of the patient's reference data from every other reference measurement made on that subject in a round-robin fashion.

In a further alternative processing method, the generic calibration data are created by subtracting some linear combination of spectral library data in order to minimize inter-subject spectral features. Subject-specific attributes can be reduced by subtracting some linear combination of similar spectra. That is, the subject-specific subtrahend for a given subject consists of a linear combination of spectra obtained from one or more subjects each of whom are different than the given subject. In one embodiment, the spectrum of a given subject would be matched with a combination of similarly appearing spectra from other subjects. In another embodiment, one would match the spectrum of a given subject with a combination of spectra from other subjects where the matching criteria involve measurable parameters such as age, gender, skin thickness, etc.

In another alternative processing method, the generic calibration data are created through simulation in a manner that minimizes subject-specific spectral attributes. This methodology can require accurate simulations of patient spectra, as well as accurate modeling of the optical system, the sampler-tissue interface, and the tissue optical properties which all contribute to such spectral variation. Generic calibration data can be simulated directly or subject data can be simulated. The simulated subject spectra can subsequently be processed by any of the preceding five processing methods. In an additional embodiment, the simulated data can be combined with real patient data for the creation of a hybrid generic calibration data.

Once the generic calibration data have been created, such data is then utilized to create a tailored prediction process specific for a particular subject for use in future predictions of the biological attribute. The tailored prediction process can be accomplished in several ways.

A direct way to tailor the prediction process to a given subject is as follows and will be denoted as direct tailoring. First, the generic calibration data are used to develop an intra-subject calibration model for the analyte of interest. This model herein is referred to as a generic model. By design, the generic model will produce predictions that are essentially unaffected by intra-subject spectral variation that is represented in the generic calibration data and not associated with the analyte of interest. On the other hand, the generic model will produce predictions that are appropriately sensitive to the analyte of interest. The generic model is applied directly to at least one indirect measurement from a target subject for whom there are corresponding direct measurements. The resulting predictions of the generic model are averaged. The difference between the average of the direct measurements and average prediction is computed. This subject-specific difference is added to the subsequent predictions of the generic model as applied directly to the future indirect measurements from the target subject. The resultant sums comprise the net predictions of the direct measurement corresponding to the future indirect measurements from the target subject. It is important to note that a single generic model can be used in the tailoring process for a number of target subjects.

A second tailored prediction embodiment uses a combination of at least two subject reference spectra, reference analyte values and the generic calibration data to create a prediction model that is specific for use on the particular subject. The technique by which the calibration data and reference spectra are combined uses a linear combination of the data in absorbance units. The combinations of calibration data and reference data can be done in a structured or random way. It is the applicant's observation that random associations work effectively and are easily implemented. The process of creating these composite data is referred to as robustification. The resulting calibration spectra contain the reference spectra from the particular patient combined with spectral data that contains sources of spectroscopic variation associated with physiological variations, variations associated with sampling techniques, instrument variation and spectroscopic effects associated with the analyte of interest. The composite calibration data can be processed to develop a calibration model. The resulting model will be referred to hereafter as a composite calibration model. The resulting composite calibration model is specific for a particular patient and can be used to generate analyte prediction results for the particular subject.

In the use of either tailored prediction process, reference spectra and reference analyte values are utilized. The reference information is used in combination with the generic calibration data to create a tailored prediction process for use on the particular subject. In general terms the subject reference information is used to tailor a general processing method for use on a particular subject. In an additional embodiment, the subject reference spectra can be replaced by the use of a subject-matched spectrum or a set of matched spectra. Matched spectra are spectra from another subject or a combined spectrum that interacts with the calibration model in a manner similar to the subject to be predicted upon. In use, a never-before-seen subject is tested and at least one spectrum is obtained. The resulting spectrum is used for generating a prediction result and as a reference spectrum. In use and in contrast to the two prior embodiments no reference analyte value is used or needed. The implementation of this method involves the following:

Identification or creation of a matched spectra through use of the reference spectra.

Replacement of the reference spectra with the corresponding matched spectra.

Although reference analyte values are not obtained from the never-before-seen patient, matched analyte values from the corresponding matched spectra are used in the processing method in a manner consistent with the prior uses of reference analyte values.

Use of either tailored prediction process.

In practice, the spectral data from the never-before-seen subject is compared with spectral data that has corresponding biological attribute reference values in a spectral library to identify the best method or several matched spectra. Matched spectra are spectra from another subject that appear similar when processed by the calibration model. Applicants have observed that identical twins are well matched from a spectroscopic model perspective.

As stated previously, the application of known multivariate analysis techniques have not resulted in glucose prediction results at a clinically relevant level. The processing method described overcomes these known limitations by using a matched spectrum. Thus, the subject tailoring with this method is accomplished without an actual reference analyte value from the individual. The matched spectrum method in conjunction with either tailored prediction process can require a large spectral library to facilitate the appropriate matching between the subject to be predicted upon and at least one library spectrum. In implementation of this matching method, applicants have identified matched spectra by finding those spectra that are most consistent with the calibration model as reflected by such parameters as Mahalanobis distance and spectral residual metrics. Other methods of spectral match would also have applicability for determination of matched spectra.

These and various other advantages and features of novelty that characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views:

FIG. 13 graphically depicts the ability of the present invention to transfer calibration using direct tailoring with two-instrument master calibration; and FIG. 14 graphically depicts the ability of the present invention to transfer calibration using composite tailoring with two-instrument master calibration.

DETAILED DESCRIPTION

Figure 1:
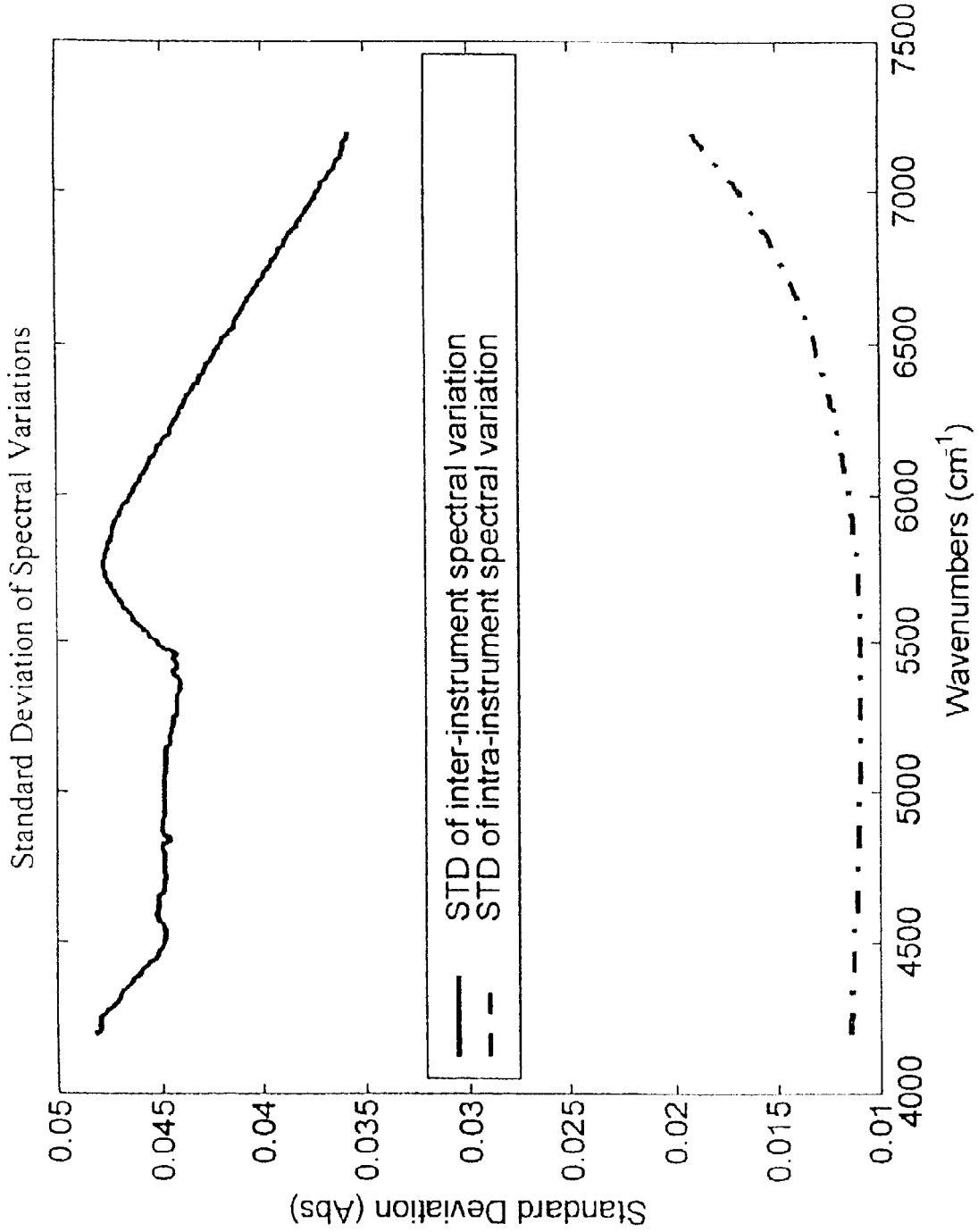
FIG. 1 depicts exemplary spectral variation observed in instruments.

Detailed descriptions of embodiments of the present invention are disclosed herein. However, it is to be understood that the disclosed embodiments are merely exemplary of the present invention that can be embodied in various systems. Therefore, specific details disclosed herein are not to be interpreted as limiting, but rather as a basis for the claims and as a representative basis for teaching one of skill in the art to variously practice the invention.

The present invention is directed to a method for optical measurement of attributes in a biological sample such as tissue analytes or properties using spectroscopy. In a preferred embodiment for noninvasive glucose monitoring, the sample is a complex matrix of materials with differing refractive indices and absorption properties. Further, because the tissue or blood constituents of interest are present at very low concentrations, it has been found necessary to incorporate a mathematical model derived using multivariate analysis. The ability to transfer this calibration model from a master instrument or master instruments to a slave instrument in a simple manner and with minimal loss in predictive performance has not been previously demonstrated. The present invention solves these deficiencies via improvements in experimental protocols and data analytic procedures. Experimental protocols have been improved in the sense that the acquisition of a wide variety of intra-instrument spectral variation is emphasized. Coinciding with the improved protocols are data analytic methods that modify the calibration data to reduce instrument-specific spectral attributes that are unrelated to measuring the biological attributes of interest. The resulting modified calibration data set thus facilitates the development of models that perform well in the presence of actual within-instrument variation. The prediction methodologies using this core concept are detailed below, subsequent to a description of the method and apparatus used for non-invasive measurement in conjunction the model.

The present invention utilizes light energy in the near-infrared region of the optical spectrum as an energy source for analysis. Water is by far the largest contributor to absorption in tissue in the near-infrared region because of its concentration, as well as its strong absorption coefficient. It has been found that the total absorption spectrum of tissue, therefore, closely resembles the water spectrum. Less than 0.1 percent of the absorption of light is from, for instance, a constituent such as glucose. It has been further found that tissue greatly scatters light because there are many refractive index discontinuities in a typical tissue sample. Water is perfused through the tissue, with a refractive index of 1.33. Cell walls and other features of tissue have refractive indices closer to 1.5 to 1.6. These refractive index discontinuities give rise to scatter. Although these refractive index discontinuities are frequent, they are also typically small in magnitude and the scatter generally has a strong directionality toward the forward direction.

This forward scatter has been described in terms of anisotropy, which is defined as the cosine of the average scatter angle. Thus, for complete backward scatter, meaning that all scatter events would cause a photon to divert its direction of travel by 180 degrees, the anisotropy factor is −1. Likewise, for complete forward scatter, the anisotropy factor is +1. In the near-infrared, tissue has been found to have an anisotropy factor of around 0.9 to 0.95, which is very forward scattering. For instance, an anisotropy factor of 0.9 means that an average photon of light only scatters through an angle of up to 25 degrees as it passes through the sample.

In analyzing for an analyte in tissue, measurements can be made in at least two different modes. It is recognized that one can measure light transmitted through a section of tissue, or one can measure light reflected, scattered or remitted from tissue. It has been recognized that transmission is the preferred method of analysis in spectroscopy because of the forward scattering of light as it passes through the tissue. However, it is difficult to find a part of the body which is optically thin enough to pass near infrared light through, especially at the longer wavelengths. Thus, the preferred method for measurement in the present invention is to focus on the reflectance of light from the sample. Preferred apparatus and methods for conducting such measurements are disclosed by Robinson in U.S. Pat. No. 5,830,132, the disclosure of which is incorporated herein by reference.

In preferred embodiments of an apparatus for non-invasively measuring a biological attribute such as a blood analyte concentration, several elements are combined in conjunction with a mathematical model. The apparatus generally includes three elements, an energy source, a sensor element, and a spectrum analyzer. The sensor element preferably includes an input element and an output element, which can include a single lens system for both input and output light energy, as for example a fiber optic bundle. The input element and output element are in contact with a common skin surface of an analyte-containing tissue. In an alternative embodiment, an alternative sensor element arrangement is used, wherein the input element and output element are arranged on opposing surfaces of an analyte containing tissue. Both embodiments function to give a measure of the absorption of infrared energy by the analyte-containing tissue. However, the first embodiment is utilized to measure the quantity of light energy that is reflected from the analyte-containing tissue by the analyte components therein. In contrast, the second embodiment measures the transmission of light energy through the analyte-containing tissue. In either embodiment, the absorption at various wavelengths can be determined by comparison to the intensity of the light energy from the energy source.

The energy source is preferably a wide band, infrared black body source. The optical wavelengths emitted from the energy source are preferably between 1.0 and 2.5 µm. The energy source is operatively coupled to a first means for transmitting infrared energy from the energy source to the input element. In preferred embodiments, this first means can simply include the transmission of light energy to the input element through air by placing the energy source proximate the input element or use of a fiber optic cable.

The input element of the sensor element is preferably an optical lens or fiber that focuses the light energy to a high energy density spot. However, it is understood that other beam focusing means can be utilized in conjunction with the optical lens to alter the area of illumination. For example, a multiple lens system, tapered fibers, or other conventional optical beam-shaping devices could be utilized to alter the input light energy.

In both embodiments, an output sensor is utilized to receive reflected or transmitted light energy from the analyte containing tissue. As described in conjunction with a method of analysis below, the first embodiment has an output sensor that receives reflected light energy, while the second embodiment includes an output sensor which receives transmitted light through the analyte-containing tissue. As with the input element, the output element is preferably an optical lens or fiber optic. Other optical collection means can be incorporated into an output element, such as a multiple lens system, tapered fiber, or other beam-collection means to assist in directing the light energy to the spectrum analyzer.

A second means for transmitting infrared energy is operatively connected to the output element. The light transmitted through the second means for transmitting infrared energy is transmitted to the spectrum analyzer. In a preferred embodiment, the operative connection to the output element includes transmission of the reflected or transmitted light energy exiting the output element through a fiber optic or air to the spectrum analyzer. A mirror or series of mirrors can be utilized to direct this light energy to the spectrum analyzer. In a preferred embodiment, a specular control device is incorporated to separate the specular reflected light from diffusely reflected light. This device is disclosed in co-pending and commonly assigned application Ser. No. 08/513,094, filed Aug. 9, 1995, and entitled "Improved Diffuse Reflectance Monitoring Apparatus," now U.S. Pat. No. 5,636,633, issued Jun. 10, 1997, the disclosure of which is incorporated herein by reference.

In practicing a preferred method of the present invention, an analyte-containing tissue area is selected as the point of analysis. A preferred sample location is the underside of the forearm. The sensor element, which includes the input element and the output element, is then placed in contact with the sample area.

In analyzing for a biological attribute, such as for the concentration of glucose in the analyte-containing tissue, light energy from the energy source is transmitted through the first means for transmitting infrared energy into the input element. The light energy is transmitted from the input element to the skin surface. The light energy contacting the skin surface is differentially absorbed by the various components and analytes contained below the skin surface within the body (i.e., blood within vessels) therein. In a preferred embodiment, the non-absorbed light energy is reflected back to the output element. The non-absorbed light energy is transmitted via the second means for transmitting infrared energy to the spectrum analyzer.

In a preferred embodiment, a biological attribute, such as the concentration of glucose in the tissue, is determined by first measuring the light intensity received by the output sensor. These measured intensities in combination with a calibration model are utilized by a multivariate algorithm to predict the glucose concentration in the tissue. In preferred embodiments, the calibration model empirically relates the known biological attribute in the calibration samples to the measured intensity variations obtained from the calibration samples. The spectrum analyzer of the present invention preferably includes a frequency dispersion device and photodiode array detectors in conjunction with a computer to apply the data received from such devices to the model stored therein to predict the biological attribute of interest of the subject.

As previously stated, the computer includes a memory device having stored therein a multivariate calibration model empirically relating known biological attributes, such as glucose concentration, in a set of calibration samples to the measured intensity variations from the calibration samples, at several wavelengths. The model can be stored as calibration data which can include spectra and direct reference values. The memory device can also store reference measurement information and indirect measurement information to be used in a prediction process. As previously stated, this data can be stored in raw or processed form which can include raw data, a calibration model, an eigenvector decomposition of the data, or any other suitable representation of the data. The memory device can be any known device. The present invention includes prediction methodologies with sufficient accuracy to act as a surrogate predictor of biological attributes so that direct measurements can be dramatically reduced or eliminated.

Generally, the method of the present invention uses a master calibration developed from one or multiple master instruments in combination with instrument-specific data to create a tailored prediction process. The resulting instrument-tailored prediction process combines selected portions of multiple instrument spectral variances and instrument reference spectra. The tailored prediction process is made instrument-specific by incorporating a minor amount of instrument-specific spectral data and does not require extensive calibration testing of the individual instrument on which the model is to be applied. The various embodiments described below can require data collection and processing to be applied in both a calibration and a prediction phase.

In the calibration phase, the methods generally require the realization of calibration data that has been modified in such a way as to reduce or eliminate instrument-specific spectral attributes that are unrelated to the biological attribute of interest in the test. The resulting modified calibration data has reduced inter-instrument spectroscopic variation while maintaining other relevant sources of spectroscopic variation. Some known sources of spectroscopic variation include changes due to illumination system, detector, data acquisition system, sampler, or spectrometer, variation associated with sampling errors, and spectroscopic effects associated with the analyte or attribute of interest. Such calibration data is referred to herein as generic calibration data.

In the prediction phase, two general embodiments are incorporated. The first method focuses on developing a model from the generic calibration data followed by introducing instrument-specific data, and utilizing this information to create an instrument-specific prediction through use of the generic model. The second general approach includes incorporating instrument-specific data from an individual instrument to be tested along with the generic calibration data. The resulting composite data is used in the multivariate analysis to generate a prediction function. The prediction function resulting from the combination of generic calibration data and instrument-specific data is a composite calibration model that is instrument specific.

In all embodiments, a model is developed using spectroscopic variation from one or more instruments that represent multiple instrument states wherein the tailored prediction method uses one or more reference spectroscopic measurements from a specific instrument so that the prediction process becomes instrument tailored for that specific instrument. Applicants have found that the resulting calibration model is an accurate predictor because it incorporates variation from other instruments to enhance or strengthen a calibration for subsequent use on a given instrument. The prediction procedure results in a method that is specific for use on a given instrument, but where information not from the instrument is used to enhance prediction accuracy, in combination with spectral information from that particular instrument.

In practicing the present invention, the first step of one preferred method is to generate generic calibration data that is essentially free from instrument-specific effects. This step can be accomplished by utilizing a device such as disclosed in the aforementioned Robinson U.S. Pat. No. 4,975,581 to indirectly measure spectra from one or many instruments, each at a variety of instrumentation conditions (such as taking recording spectra under different environmental conditions over a period of time) and instrumentation states (such as taking recording spectra with a variety of different bulbs).

Figure 2:
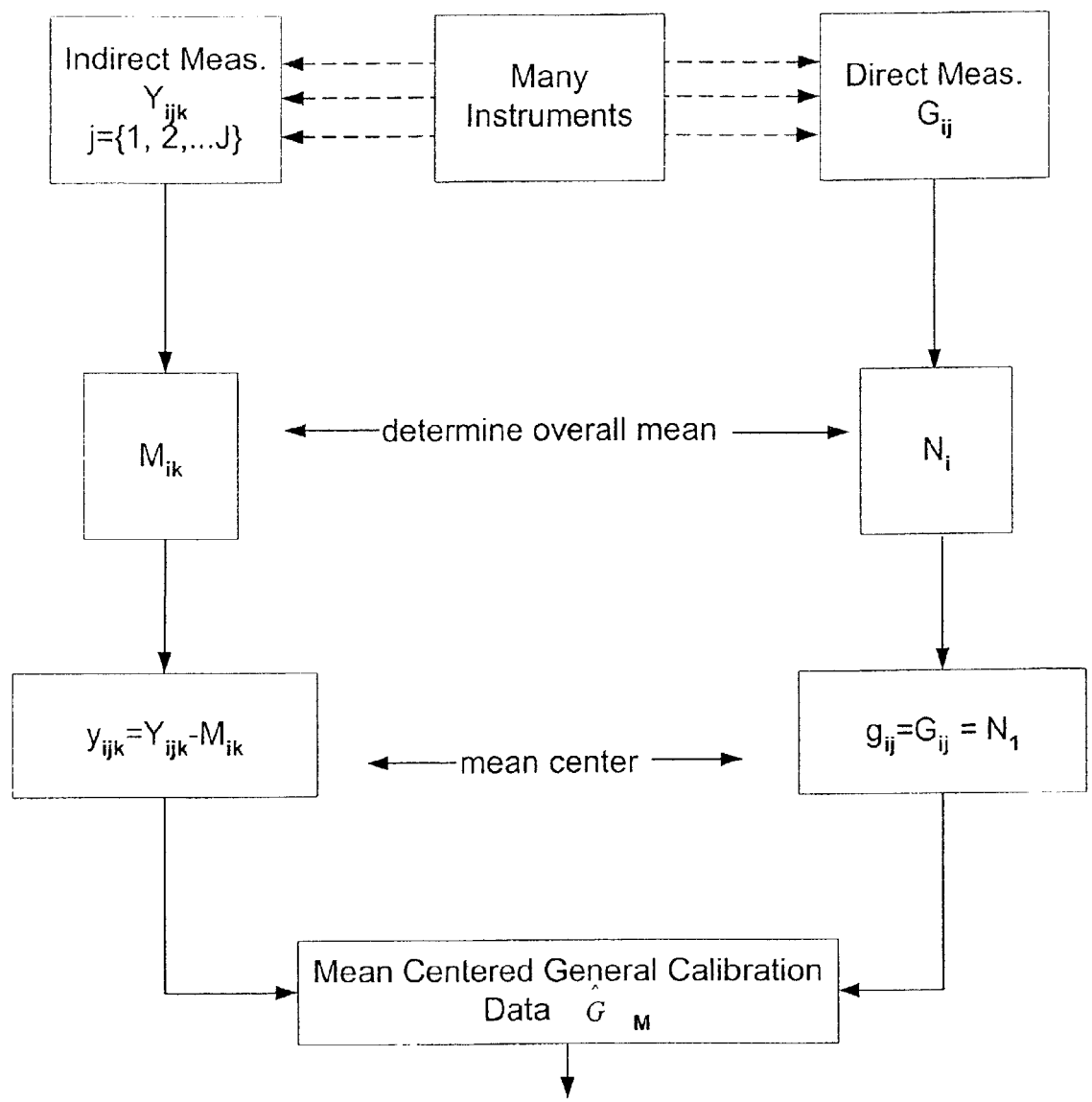
FIG. 2 is a flow chart representing the processing steps associated with generating generic calibration data through meancentering.

A preferred method to generate generic calibration data is referred to as meancentering and is depicted in the flow chart of FIG. 2. Here, let $Y_{ijk}$ be the spectral measurement (e.g., log(intensity)) of the $k^{th}$ wavelength within the $j^{th}$ spectrum from the $i^{th}$ instrument. Instrument-specific effects are removed as follows. First, form the mean spectrum for each instrument. The mean spectrum at the $k^{th}$ wavelength for the $i^{th}$ instrument is:

$$M_{ik} = \frac{1}{J_i}\sum_{J=1}^{J_i} Y_{ijk}$$

where $J_i$ is the number of spectra from the $i^{th}$ instrument. The appropriate mean spectrum is then removed from each observed spectrum: $y_{ijk}=Y_{ijk}-M_{ik}$. This process can be referred to as meancentering the spectra by instrument.

Associated with each spectrum, we also have a direct measurement of reference blood-analyte concentration, $G_{ij}$. The analyte concentrations are also meancentered by instrument, resulting in $g_{ij}=G_{ij}-N_i$, where $N_i$ is the mean analyte concentration for the $i^{th}$ instrument and defined as:

$$N_i = \frac{1}{J_i}\sum_{J=1}^{J_i} G_{ij}$$

The meancentered analyte values can be scaled by an instrument-specific factor (k) that is equal to the relative magnitude of the spectral effect of 1 mg/dL of analyte for that instrument. This scaling serves to normalize analyte signals across instruments that could be different across instrument (e.g., due to pathlength differences) to a standard in vivo analyte signal. In terms of excess prediction errors, the use of the instrument-specific factor, k, allows the excess prediction error due to slope errors to be minimized, while meancentering predominately reduces the excess prediction error due to bias. The particular example of meancentered processing is cited to illustrate a specific processing embodiment of the invention. It is recognized that the use of this invention can involve generation of generic calibration date through multiple processing means. Instrument-specific spectroscopic variances can be reduced by subtracting (in absorbance units, or performing a similar operation in any other data space) some linear combination of each instrument's reference spectra and reference analyte values. At this point, the meancentered spectra and meancentered (and possibly scaled) analyte concentrations are used in the multivariate calibration model development.

Once the generic calibration data has been created, such data are then utilized in forming a tailored prediction process for a particular instrument for use in future predictions of the biological attribute. This can be accomplished in several ways, such as use of a direct-tailoring technique, or alternatively, a composite technique. Common to both methods is a calibration model. A representation of a linear multivariate calibration model (a specific type of calibration model) is $\hat{G}=b_0+b_1 \cdot y_1+b_2 \cdot y_2+ \ldots +b_q \cdot y_q$, where the $b_k$'s are model parameters. Development of $\hat{G}$ from the meancentered indirect data $y_{ijk}$ or other generic calibration data and the direct data $g_{ij}$ is a routine matter for one skilled in chemometrics, as taught by H. Martens et al., *Multivariate Calibration*, (1989), John Wiley, Chichester.

Note that the use of generic calibration data for developing the generic model in this embodiment is believed important for preserving sufficient sensitivity to detect outlier (or anomalous) spectra during prediction. Without the meancentering operation of the invention on the spectra, Mahalanobis-distance and other outlier detection metrics are likely to be based heavily on ancillary inter-instrument effects and, therefore, not be sufficiently responsive to unusual intra-instrument effects.

Once the generic model is in hand, it can be tailored (or adapted) for a specific instrument. Two direct tailoring versions of this procedure are described for the present embodiment. In the first version, it is assumed that the scale factor, k, pertaining to the relative magnitude of the spectral effect of 1 mg/dL of analyte is known with adequate precision. In the second version, it is assumed that this scale factor is unknown and can be estimated.

Tailoring Version 1 (K Known)

1. Make one (or several) spectral measurement with the slave instrument. Denote the resultant spectrum (or average spectrum when multiple spectra are obtained) by $Y_{ref}$, where $Y_{ref} = \{y_{r1}, y_{r2}, \ldots, y_{rq}\}$. The idea is to obtain very precise spectral measurements for the adaptation process.

2. As close as possible in time with respect to the collection of the spectrum (spectra), an accurate reference measurement of the analyte, $G_{ref}$, is obtained from the instrument.

3. Use the generic model developed from the master instruments(s) in conjunction with $Y_{ref}$ to obtain a raw prediction of analyte, $P_0$, that will be used as the basis to adapt the generic model to the instrument. Once steps 1–3 have been completed, spectroscopic measurements of analyte can be determined in the future as follows.

4. Obtain a new spectral measurement with the slave instrument, $$Y_{new} = \{y_{n1}, y_{n2}, \ldots, y_{nq}\}.$$

5. Apply the generic model developed for the master instrument(s) to $Y_{new}$ to obtain an unadapted prediction, $P_{new}$.

The prediction of analyte (adapted to that instrument) is $$\hat{G}_{new} = \frac{P_{new} - P_0}{k} + G_{ref}$$

Tailoring Version 2 (K Unknown)

In this format, steps 1–3 (from version 1) are performed at least twice (once when the target instrument is experiencing a relatively low analyte level, the other when the target instrument is experiencing a relatively high analyte level). At the relatively low analyte level, we obtain:

$$Y_{new}^{lo} = \{y_{n1}^{lo}, y_{n2}^{lo}, y_{n3}^{lo}, \ldots\}$$

At the relatively high analyte level, we obtain:

$$Y_{new}^{hi} = \{y_{n1}^{hi}, y_{n2}^{hi}, y_{n3}^{hi}, \ldots\}$$

As in version 1, apply the generic model to $Y_{new}$ to obtain an uncorrected prediction, $P_{new}$. The prediction of analyte (adapted to that instrument) is:

$$\hat{G}_{new} = \frac{P_{new} - P_0^{lo}}{\hat{k}} + G_{ref}^{lo}, \text{ where } \hat{k} = \frac{P_0^{hi} - P_0^{lo}}{G_{ref}^{hi} - G_{ref}^{lo}}$$

Note that it is straightforward (and perhaps desirable) to modify this technique to include more than one or two reference samples per target instrument.

In summary, the proposed prediction method of this first embodiment provides a solution to the difficulties associated with building a universal master calibration model that needs to be appropriately responsive to instrument-to-instrument spectral variation as well as spectral variation within instruments over time and space. The proposed method is illustrated in the flow chart of FIG. 3 and provides a simple instrument-specific adaptation to a generic model that is appropriately sensitive to the spectral variation within a instrument. As described, this embodiment can be used to effectively reduce excess prediction errors components due to bias and slope. Development of this type of instrument-specific model is a substantial improvement (with respect to efficiency) when compared to the development of instrument-specific models via intensive optical sampling with each slave instrument.

Figure 4:
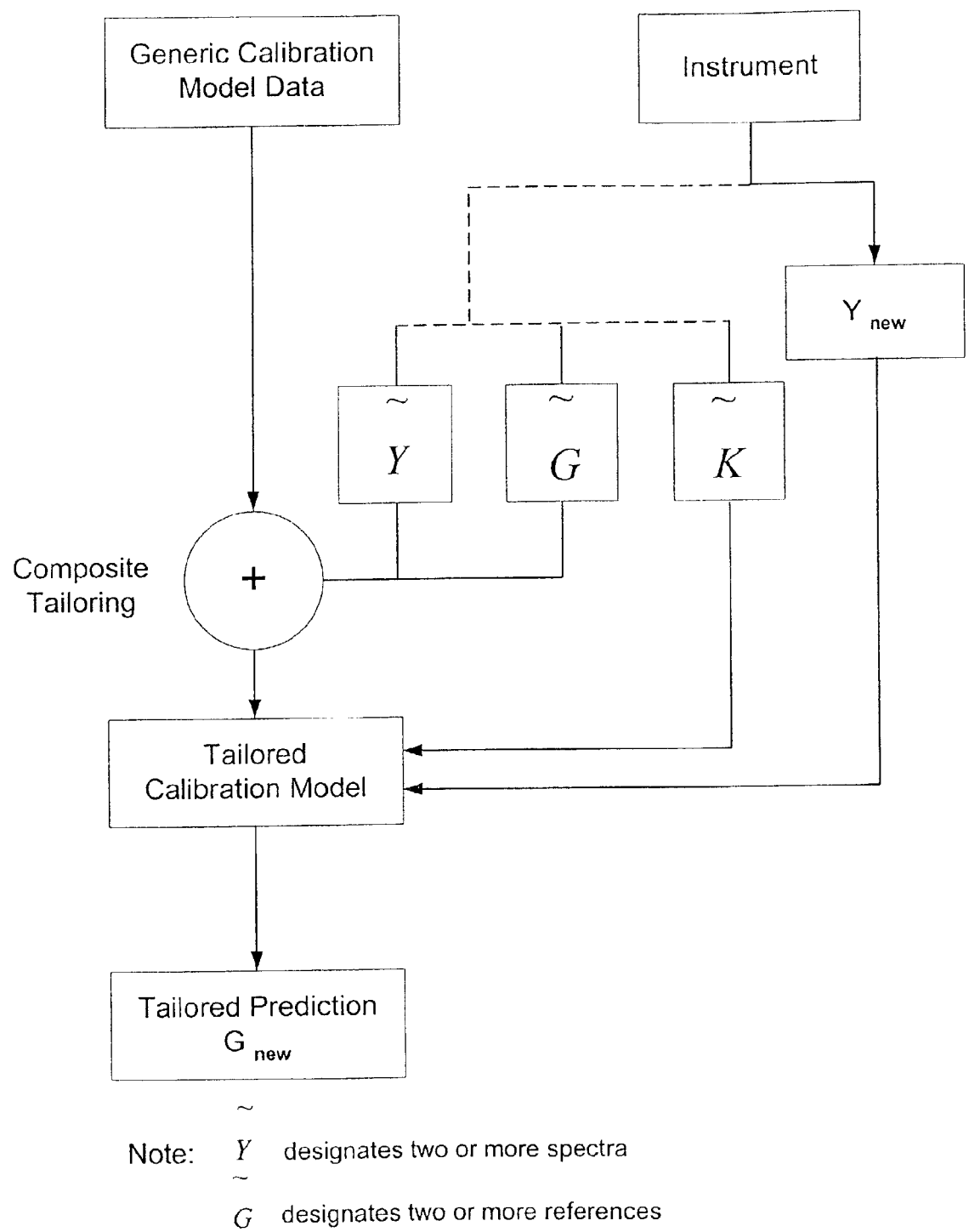
FIG. 4 is a flow chart representing the steps of the composite tailored prediction process of the current invention.

The second prediction technique of the present invention is the composite technique that is depicted in the flow chart of FIG. 4. With the composite technique, two or more reference measurements, which include both the spectra and the analyte reference values, are made on the slave instrument, and these data are added in a random fashion to the generic calibration data from the master instruments(s). This process is represented by the equations:

$$y'_{ijk} = y_{ijk} + y_{ilk}^{ref}, \quad g'_{ij} = g_{ij} + g_{il}^{ref},$$

where $y_{ilk}^{ref}$ is the $k^{th}$ element of the $l^{th}$ reference spectrum for instrument i, $g_{il}^{ref}$ is the $l^{th}$ glucose reference value for instrument i, and a random value of l is chosen for each i, j pair.

The resulting composite data is then used in conjunction with a multivariate analysis technique to generate a calibration model which is instrument tailored due to the addition of reference spectral measurements and reference analyte measurements prior to generating the model. The resulting instrument-tailored model is then applied to other spectra from the same slave instrument on whom the reference measurements were made. Predictions are made with the resulting calibration model by following standard chemometric practices known to one skilled in the art. As described, this embodiment can be used to effectively reduce excess prediction errors components due to bias, slope and precision.

Figure 5:
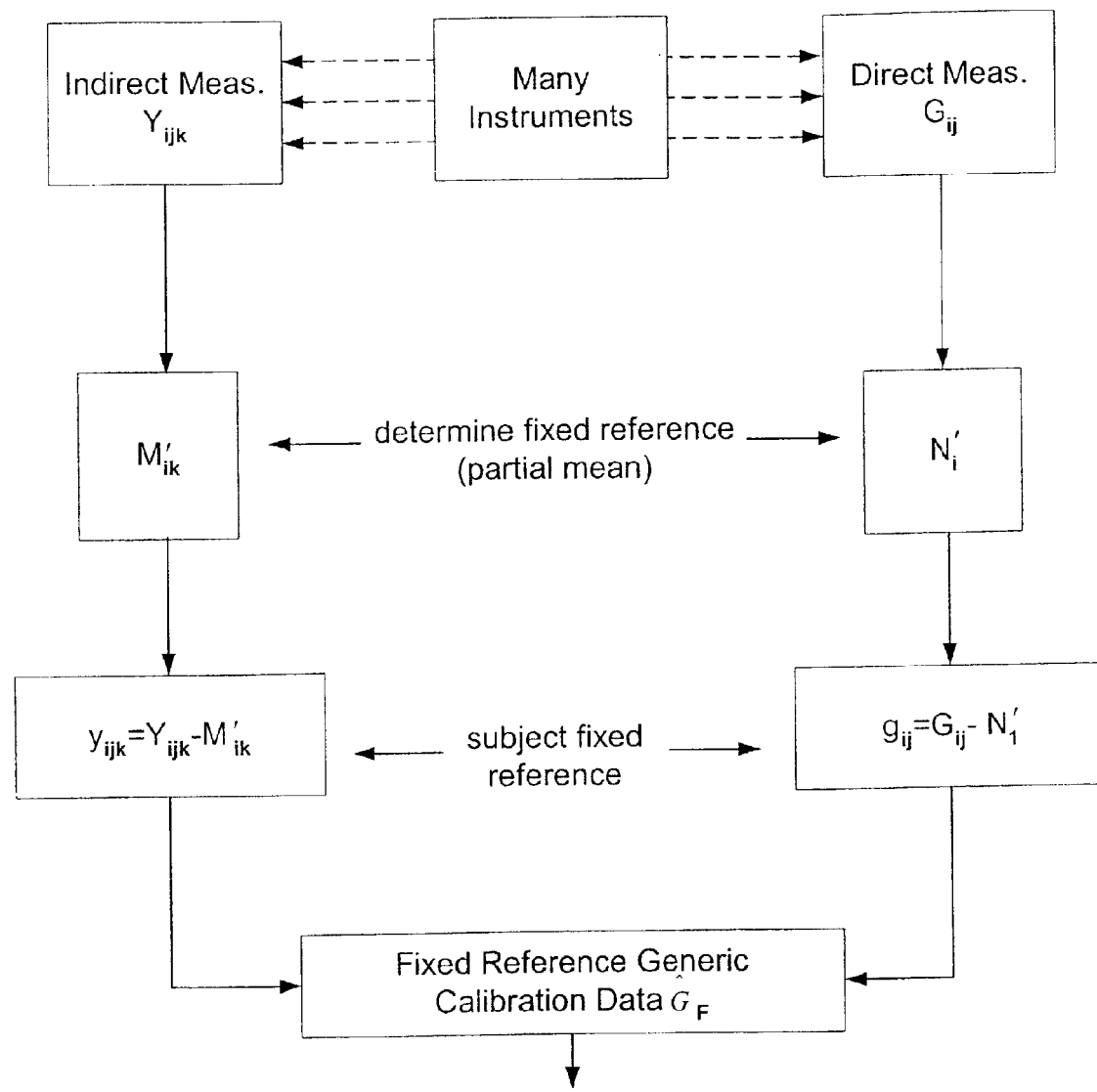
FIG. 5 is a flow chart representing the processing steps associated with generating generic calibration data through the fixed reference method.

Generic calibration data can also be created by a fixed reference technique. The fixed reference technique is depicted in the flow chart of FIG. 5. This technique can be utilized to modify master calibration data by subtracting the mean of the first S calibration spectra and reference values from a particular instrument from each of the instrument's reference measurements, where S is less than the total number of reference measurements made on a particular instrument. This is represented by the equations:

$$M_{ik} = \frac{1}{S}\sum_{j=1}^{S} Y_{ijk}, \quad N_i = \frac{1}{S}\sum_{j=1}^{S} G_{ij},$$

where $S < J_i$

In the alternative, a moving window reference technique can be utilized wherein you subtract the mean of the S nearest (in time) calibration spectra and reference values from each of the instrument's calibration measurements, where S is less than the total number of reference measurements made on a particular instrument. This method is represented by the equations:

$$M_{ijk} = \frac{1}{S}\sum_{l=J-\left(\frac{S-1}{2}\right)}^{J+\left(\frac{S-1}{2}\right)} Y_{ijk}, \quad N_{ij} = \frac{1}{S}\sum_{l=J-\left(\frac{S-1}{2}\right)}^{J+\left(\frac{S-1}{2}\right)} G_{ij},$$

where S is odd

The value of S can be chosen to fit the constraints of the particular application, neglecting effects due to random noise and reference error.

Figure 6:
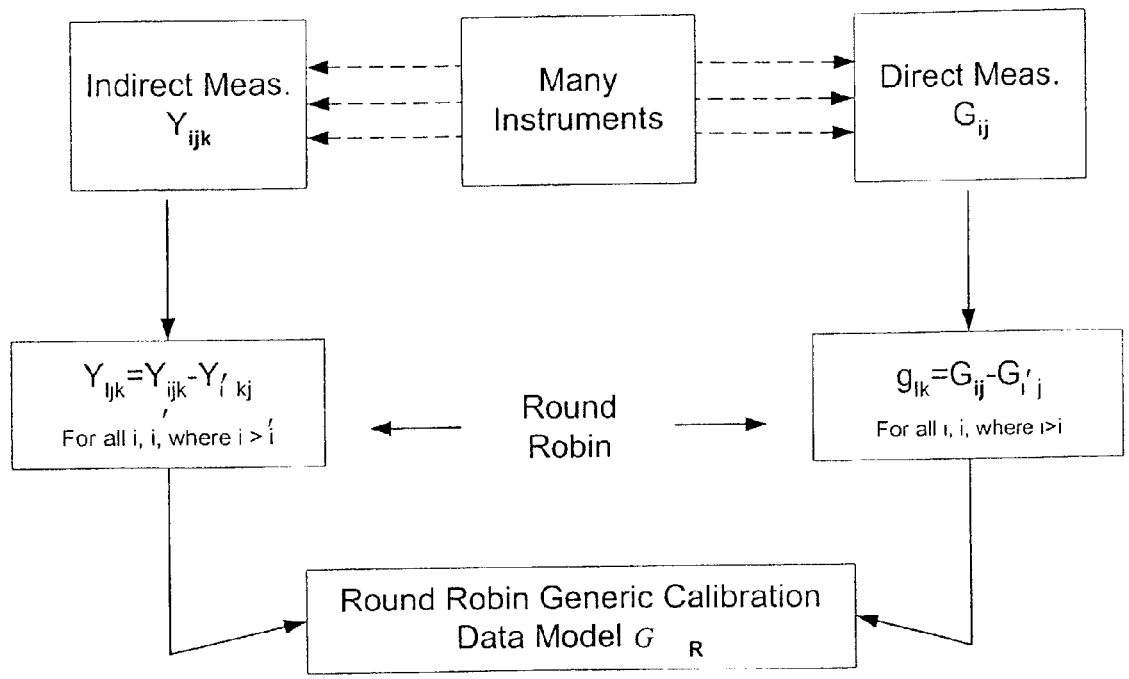
FIG. 6 is a flow chart representing the processing steps associated with generating generic calibration data through the round-robin method.

Alternatively, the generic calibration data can be generated in a round-robin reference manner wherein you subtract each of the instrument's reference data from every other reference measurement made on that instrument in a round-robin fashion. The round-robin method is depicted in the flow chart of FIG. 6. This method is represented by the equations:

$$y_{ilk} = Y_{ij_lk} - Y_{ij'_lk}$$
$$g_{il} = gij_l - gij'_l$$

For all j, j' where j'$_l$>j$_l$

Figure 7:
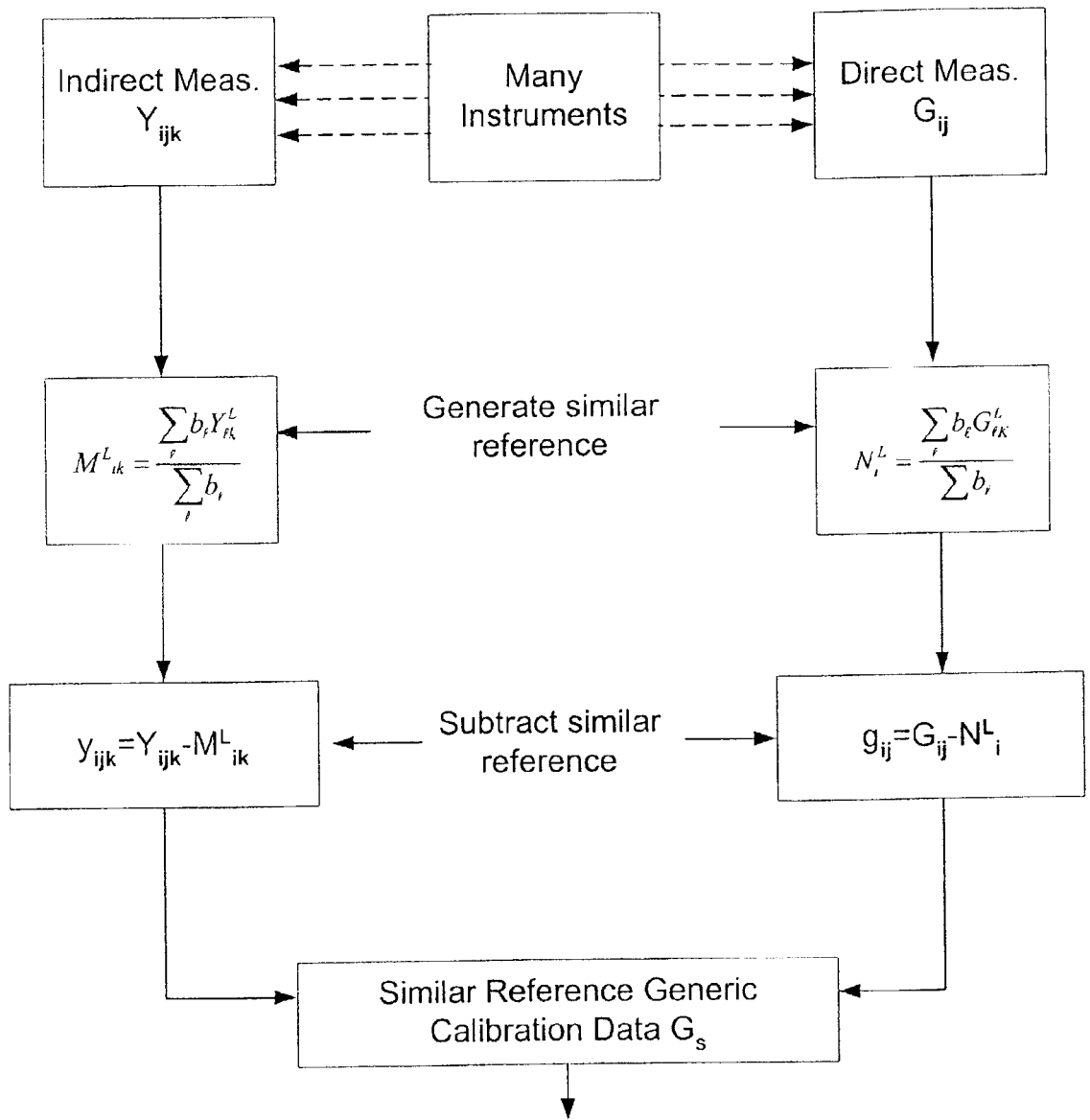
FIG. 7 is a flow chart representing the steps of the composite tailored prediction process of the current invention.

Another method used for generating generic calibration data can be useful where a large spectral library, including spectra and reference values from multiple instruments, exists. The library data are modified to reduce or eliminate instrument-specific spectral attributes by subtracting some linear combination of spectral library data in order to minimize cross-instrument spectral features. The methods of this embodiment are depicted in the flow chart of FIG. 7. Thus, in modifying the spectral library data to create generic calibration data, a given instrument's spectra are modified through the use of a similar instrument spectra. Similar instrument spectra are those spectra that when subtracted from a specific instrument results in a spectral difference that is less than the average difference across all instruments. The similar spectrum can be from another instrument or can be formed by combining several instruments to create a similar spectrum.

In an additional embodiment, instrument spectra are created through simulation in a manner that minimizes instrument-specific spectral attributes. This methodology requires accurate simulations of sample spectra, which would include high accurate modeling of the optical system, the sampler interface, and the optical properties of the sample which all contribute to such spectral variation. Such simulated data can be generated and removed from measured calibrated data to reduce instrument-specific characteristics. The modified calibration model data can then be utilized in conjunction with data from a specific instrument to tailor the model for use in predicting analytes, such as glucose in tissue.

Once the generic calibration data have been created, such data are then utilized in forming a tailored prediction process for a particular instrument for use in future predictions of the biological attribute. This can be accomplished in several ways, such as use of the direct-tailored technique, or alternatively, the composite technique previously described.

Figure 8:
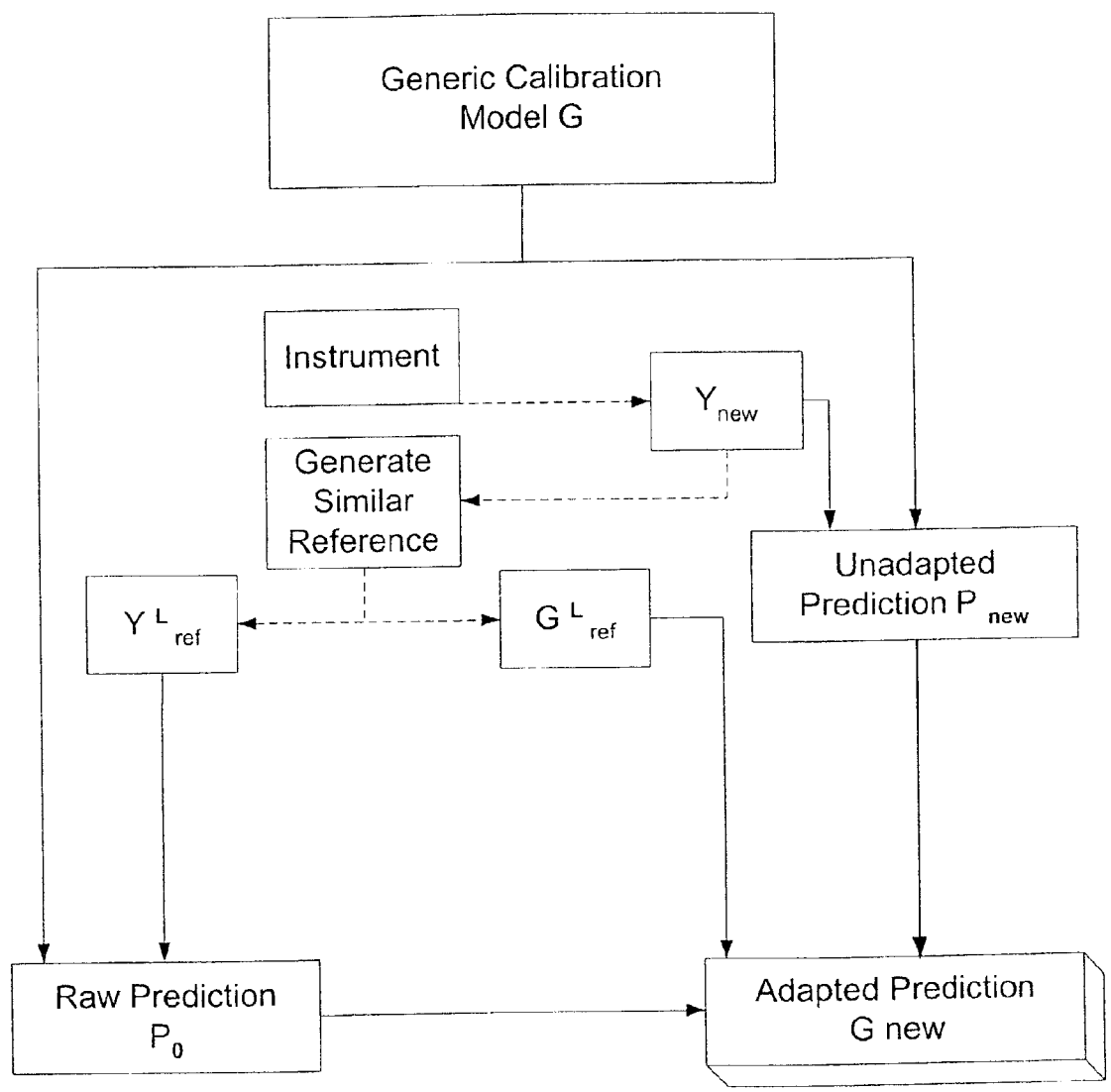
FIG. 8 is a flow chart representing the steps of the matched spectrum method in conjunction with the direct-tailored prediction process of the current invention.
Figure 9:
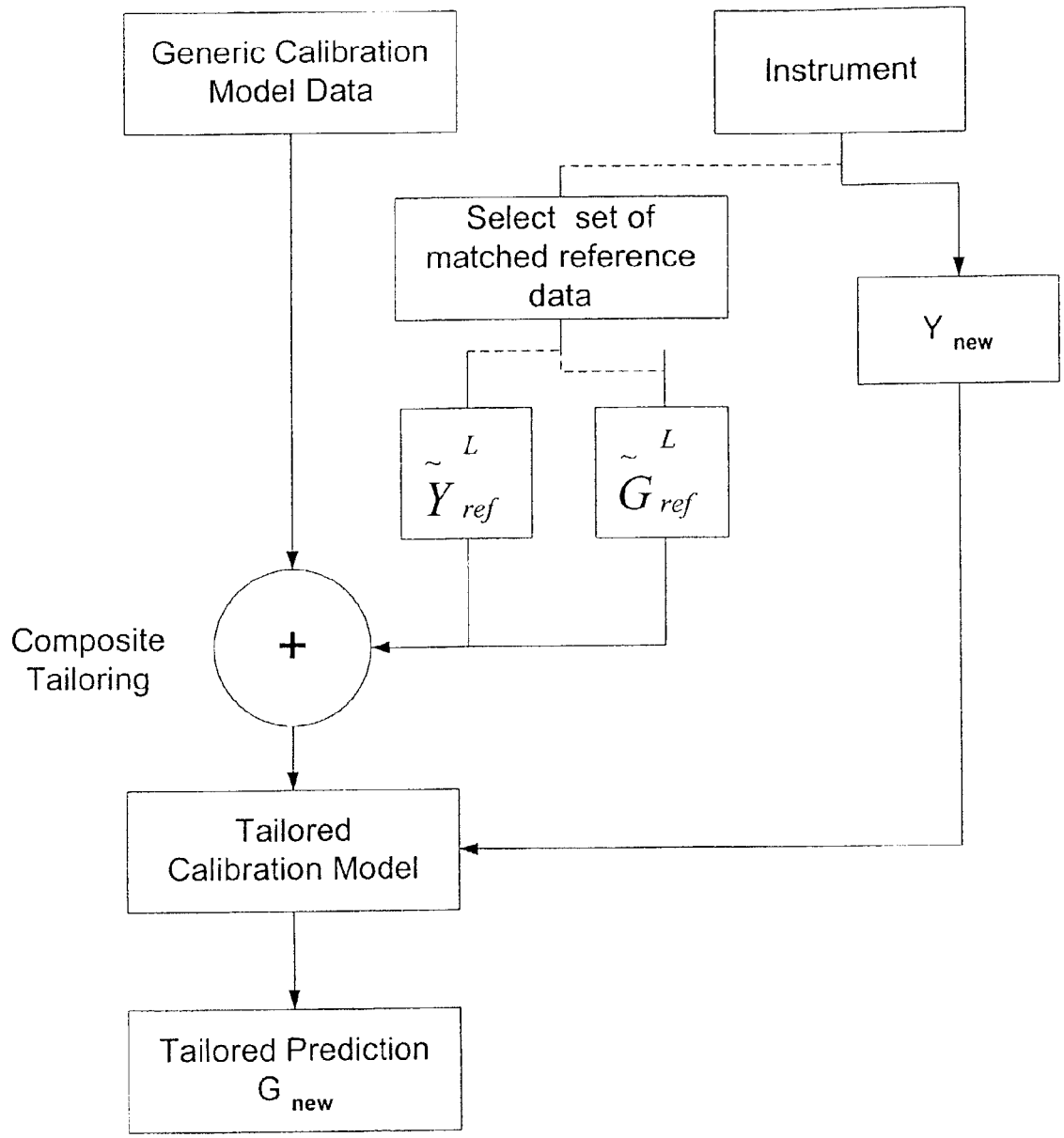
FIG. 9 is a flow chart representing the steps of the matched spectrum method in conjunction with the composite tailored production process of the current invention.
Figure 10:
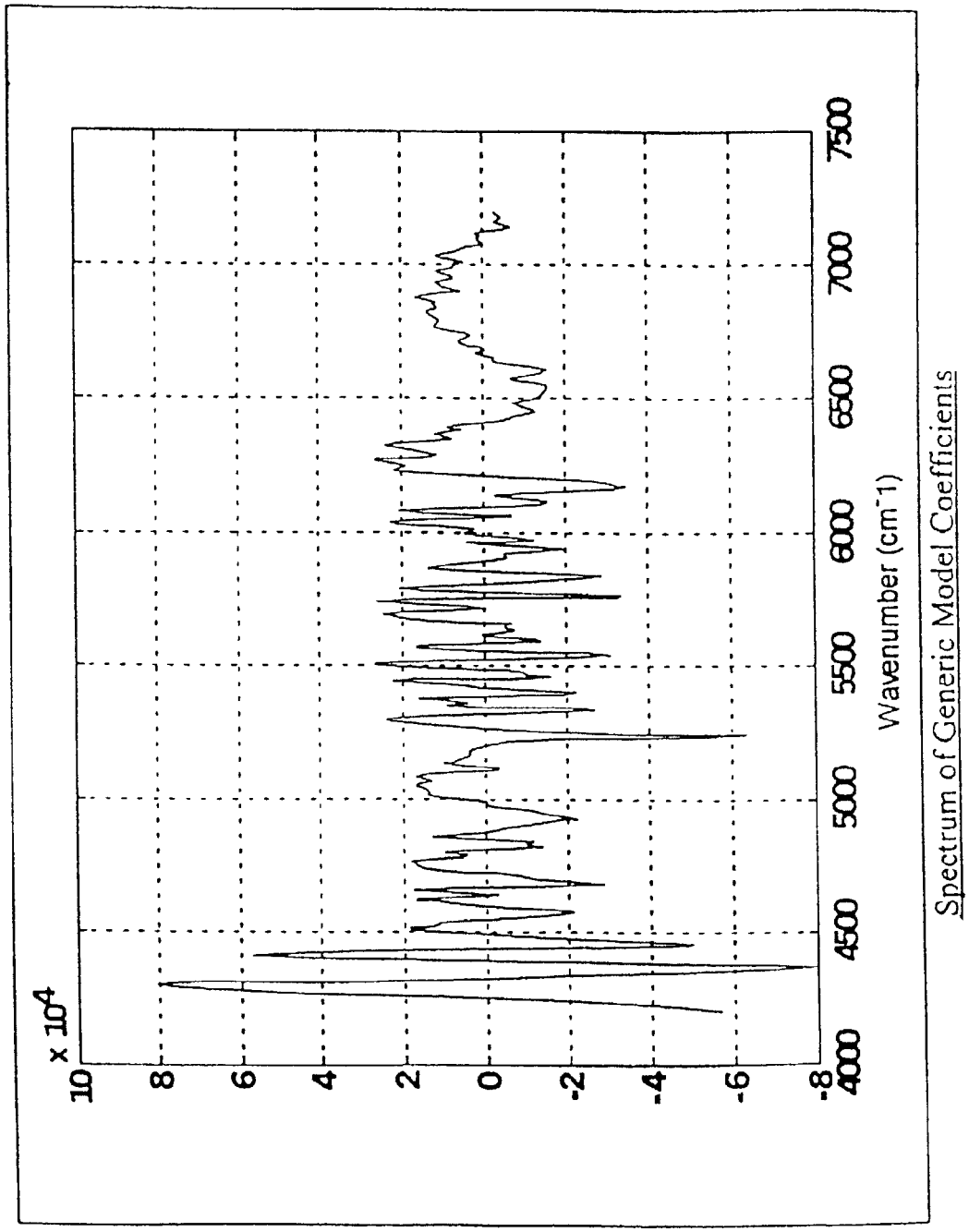
FIG. 10 displays the spectrum of generic model coefficients.

With either the direct-tailored prediction method or the composite tailored prediction method as previously described, the reference spectra can be replaced by matched spectra. The flow charts of FIGS. 8 and 9 depict matched spectra methods with direct tailored prediction and composite tailored prediction, respectively. With this method, a never-before-seen instrument is then tested and at least one target spectrum or set of spectral data is acquired. However, no analyte or direct measurement is required in conjunction with the spectral measurement. Rather, the spectral data from the never-before-seen instrument is compared with spectral data which has corresponding attribute reference values in a spectral library to identify the best reference spectrum or spectra that corresponds to the target spectrum of the never-before-seen instrument. This reference spectrum can be compared with the target spectrum to determine the level of match. Thus, the instrument tailoring with this method is accomplished without an actual reference analyte value. This method relies on a large spectral library to facilitate the appropriate matching between a target spectrum and a single spectral library entry or several library entries.

In the direct-tailored prediction method, the matched spectrum and corresponding reference analyte values are used instead of actual reference spectra and analyte values from the instrument to be predicted upon. The following equations define the substitution and prediction steps:

$$\hat{G}_{new} = P_{new} - P_0^{SIM} + G_{ref}^{SIM}$$

where
$P_{new}$ is the raw prediction of the new spectrum $Y_{new}$ using the generic model,
$P_0^{SIM}$ is the raw prediction of the similar spectrum $Y^{SIM}$ identified in the spectral library,
$G_{ref}^{SIM}$ is the referenced valve associated with the similar spectrum identified in the spectral library One characteristic of this methodology is the ability to find an appropriate match within the spectral library. If no single instrument is an appropriate match, a matched spectrum can be created by combining spectra from other instruments. In practice, the matched spectrum, a combination of spectra and inference values from instrument in the spectral library, is created through a weighted linear combination of absorbance spectra. The various coefficients applied to the individual library spectra can be adjusted such that the best possible match is obtained. The matched spectrum created through other instrument combinations is created by the following equations:

$$Y_K^{SIM} = \frac{\sum_{j=1}^{S} c_j y_{JK}^{SIM}}{\sum_{J=1}^{S} c_j} \quad G_{ref}^{SIM} = \frac{\sum_{j=1}^{S} c_j G_j^{SIM}}{\sum_{j=1}^{S} c_j}$$

where $y_{JK}^{SIM}$ is the $K^{th}$ element of the $J^{th}$ spectrum selected from the spectral library, $G_j$ is the corresponding reference value, and the coefficients, c, are chosen to optimize the spectral similarity with $Y_{new}$ The resulting matched spectrum and reference value is used in a manner consistent with a matched spectrum obtained from a single instrument. As described, this embodiment can be used to effectively reduce excess prediction errors components due to bias and slope.

In using the composite tailored prediction, process generic calibration data is combined with one or more reference spectra and reference values to create a data set that is subsequently used for generation of a calibration model. The reference spectra used for the composite tailored process can be replaced by matched spectra. In practice, a fixed number of best-matched spectra from the instrument library can be used as reference spectra. In an alternative method, any spectra which meet a predetermined level of matching could be used as reference spectra. In practice, the level of match has been determined by first calculating the difference between the target spectrum and the possible matched spectrum. The resulting difference spectrum is then used in conjunction with the calibration model to determine such parameters as the Mahalanobis distance and spectral residual metrics.

Once appropriate matched spectra are determined, these spectra are used in a manner consistent with the composite tailored prediction method using reference spectra from the actual instrument to be predicted upon. As described, this embodiment can be used to effectively reduce excess prediction errors components due to bias, slope and precision.

The above benefits provide significant advantage when applied to the target application of monitoring blood/glucose levels non-invasively in the home where a single instrument unit (e.g., spectrometer) is paired with a single subject. The method provides a simple calibration transfer and maintenance method. The invention enables calibration transfer by successfully migrating a master calibration model to a specific slave unit.

EXAMPLES OF METHOD

To demonstrate the technology in the preferred embodiment of home glucose monitoring, the applicants conducted a study that simulated in a reasonable manner the calibration transfer necessary for effective noninvasive glucose monitoring. In production, it is envisioned that the noninvasive glucose monitors would be produced in mass. These monitors would contain generic calibration data that would subsequently enable effective tailoring. An individual patient would purchase the monitors and an initial tailoring process would be performed prior to use. During this initial tailoring period, the individual would effectively tailor the monitor to the themselves, as well as perform calibration transfer from the master instrument(s) to their slave instrument. In a preferred use of the application for noninvasive glucose monitoring, the applicants have used the techniques disclosed in U.S. patent application Ser. No. 09/415,432, filed Oct. 8, 1999, entitled "Methods and Apparatus for Tailoring Spectroscopic Calibration Models" in conjunction with the techniques disclosed in this application. In establishing the master calibration, the spectral data obtained from the patients has been processed to reduce between-patient differences. In addition, the master calibration data has been processed to reduce between-instrument differences. The result is calibration data that has both between-patient and between-instrument differences reduced. To demonstrate the effectiveness of the techniques, a clinical study has recently been performed to demonstrate the effectiveness of this methodology for calibration transfer for the preferred application of home glucose monitoring. In this study, calibration data were obtained from 40 diabetic subjects who were repeatedly measured over a span of seven weeks on three different instruments that were constructed in a similar manner. The intent of observing the subjects for such a long period of time was to develop calibration data that spanned significant levels of natural intra-subject physiological variation (including, but not limited to, glucose variation) and sampling variation. In addition, the study protocol involved the deliberate perturbation of the spectrometer and its local environment to induce instrumental/environmental effects into the generic calibration data. These perturbations were carefully selected to span the expected long-term operating conditions of the instrument. Specifically the ambient relative humidity was varied from 10–60% (percent), external temperature from 65–80° F. (degrees Fahrenheit), and more than 10 different bulbs were used during the study. Activities such as these are extremely important for developing calibration data that adequately captures intra-instrument variation and facilitates both calibration transfer and the ability to generate valid predictions into the future.

Spectral and reference data were acquired twice per week from most subjects. A few subjects were unable to keep all of their appointments to provide spectral and reference data. During each appointment, four separate spectral measurements on the underside of the forearm on each instrument were acquired over a 15-minute period using reflectance sampling from 4200–7200 wavenumbers (389 discrete wavelengths were involved). In addition, two capillary glucose reference measurements were obtained via blood draws from each subject during each data acquisition period on each instrument. The blood draws were performed immediately before and after the acquisition of the spectral data. Time-based interpolation was used to assign an appropriate capillary glucose reference value to each spectrum.

The spectral and capillary glucose reference data were meancentered by subject and instrument to form the generic calibration data. The resulting generic calibration data has both between-subject differences as well as between-instrument differences reduced. In order to test the efficacy of the calibration transfer method disclosed, additional spectral date from 11 diabetic subjects were taken over a subsequent four-week period. As in the case of acquiring the calibration data, four separate spectral measurements on the underside of the forearm on each instrument were acquired over a 15-minute period during each data acquisition period. In addition, capillary glucose reference measurements were acquired from each of the 11 subjects during each data acquisition period on each instrument according to the protocol described earlier. Spectral and reference data were acquired four times per week, Monday, Tuesday, Wednesday and Thursday. To effectively demonstrate the calibration transfer capabilities of the method, the spectral data from the 11 patients was divided into validation data and tailoring data. Data from Mondays and Wednesdays was used for tailoring, while the remaining data was used for validation.

In order to show the effectiveness of the methodology, a control condition was used. In the control case, the calibration from the slave instrument was used to determine the concentrations of the validation samples as measured on the slave instrument. Specifically, the control condition involved using slave calibration data tailored with slave data and subsequently predicting on slave validation data. In this control condition, all of the spectral data is from the same instrument. These results can be compared with results where the calibration data is developed on a master instrument or instruments, tailored data is from the slave instrument, and predictions are made on slave validation data. The included examination will use both the direct-tailoring and composite tailoring calibration methods. FIGS. 11–14 show the effectiveness of the various calibration transfer methods described herein. As set forth previously, the present invention provides a method that reduces the level of interfering spectral variation that occurs between instruments which otherwise must be compensated for by the multivariate calibration model. FIG. 1 shows the standard deviation of all of the stable background sample spectra collected during the validation period with three different instruments. The upper line shows the standard deviation of the spectral data set before application of a technique to reduce between-instrument differences, and the lower line shows the standard deviation of the spectral data set after reducing between-instrument differences. The method used to reduce between-instrument variances in this example was meancentering the data for each instrument. This process is diagramed in FIG. 2. The methodology significantly reduces the inter-instrument spectral effects and enables a clear definition of the intra-instrument spectral effects.

Figure 3:
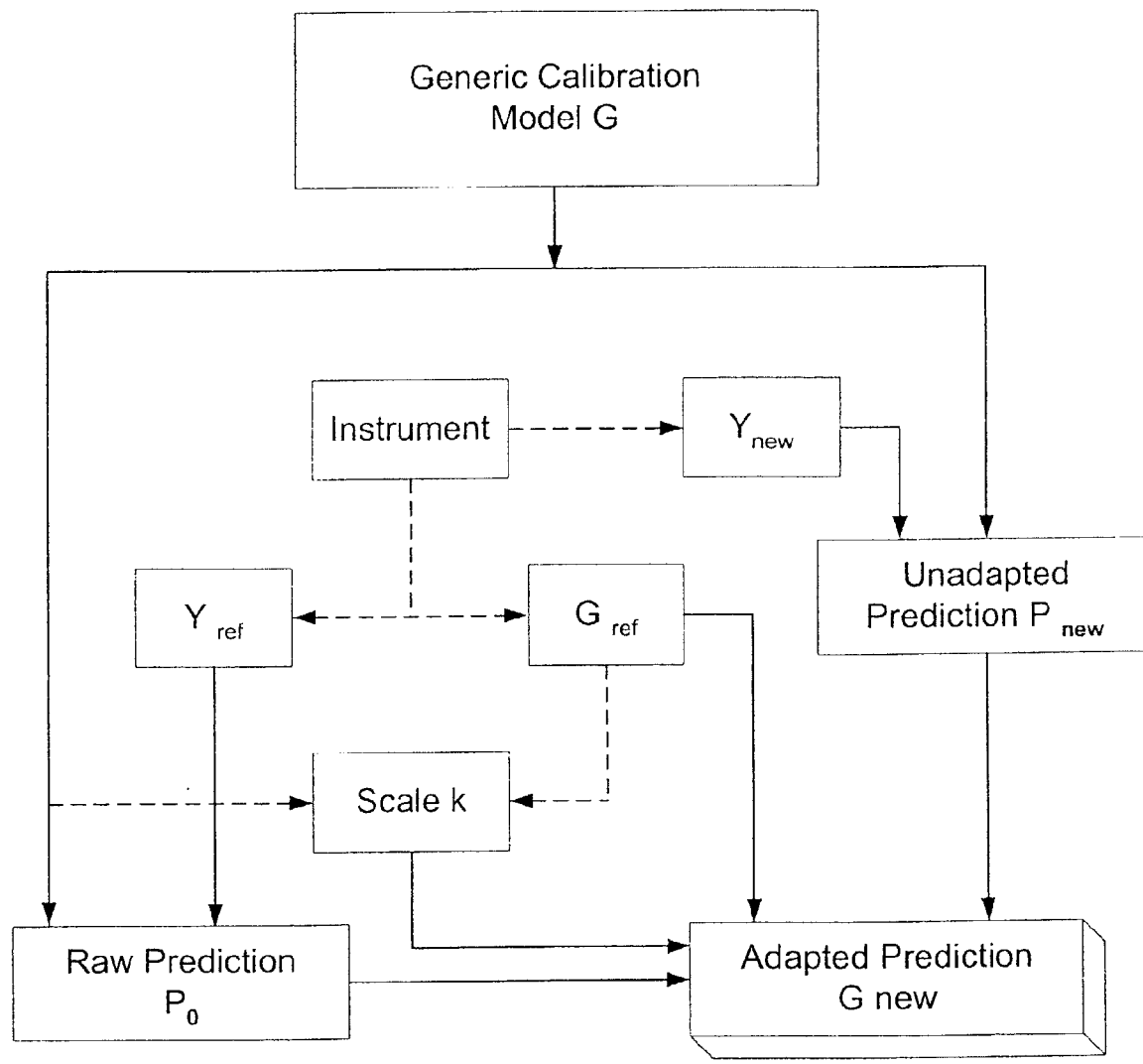
FIG. 3 is a flow chart representing the steps of the direct-tailoring prediction process of the present invention.
Figure 11:
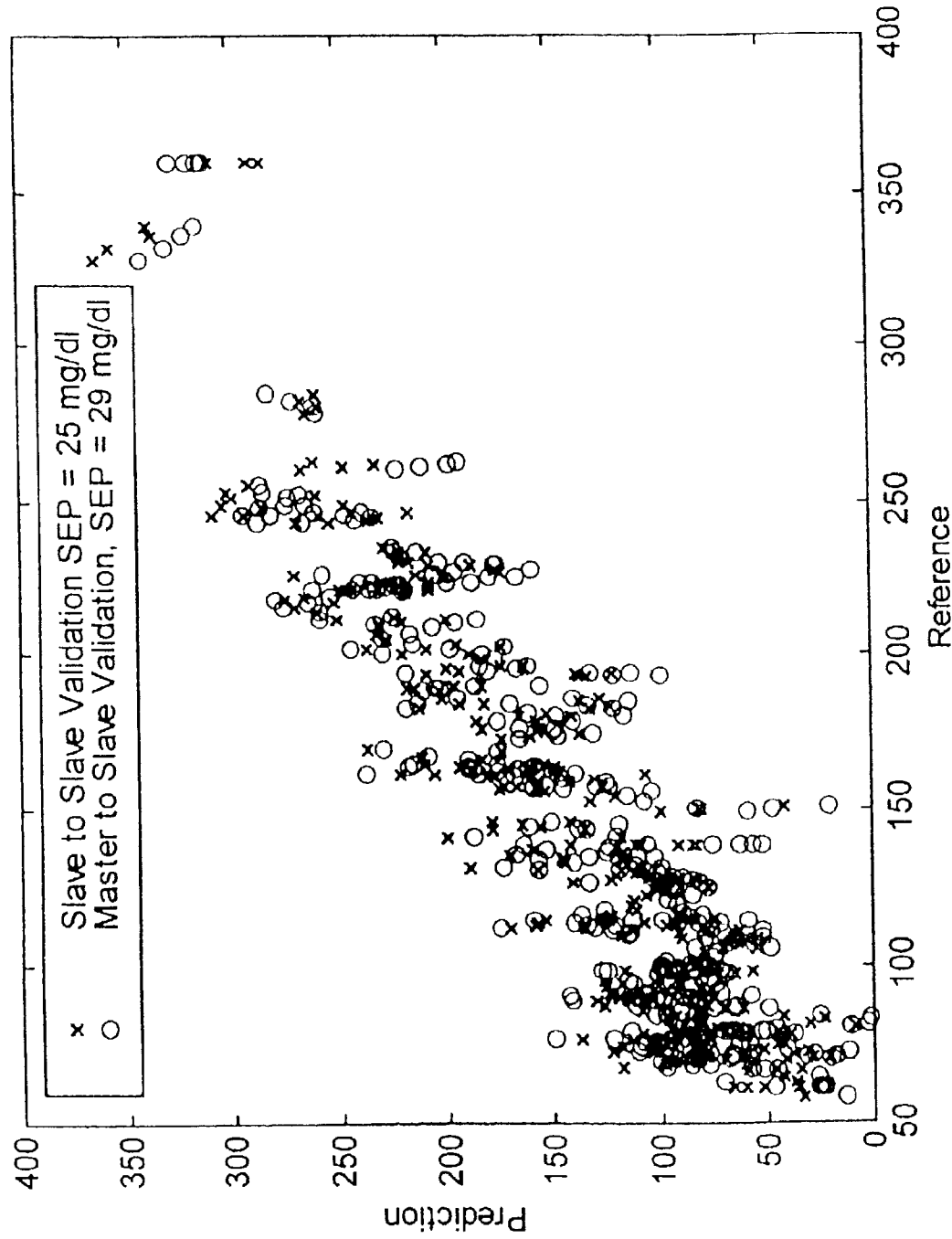
FIG. 11 graphically depicts the ability of the present invention to transfer calibration using direct tailoring.

For the first embodiment, direct tailoring, the data were processed using the tailoring method described previously, and shown in FIG. 3. The generic calibration data from a master instrument was used to develop the calibration model. The calibration model was developed using partial least squares regression. This master calibration model was subsequently tailored with spectra from an individual subject, as shown in FIG. 3. The resulting instrument and subject specific model was used to predict on the subject's validation data. The process was repeated for all 11 patients individually. The results for the direct-tailoring method for a single instrument are shown in FIG. 11. The prediction results are quite similar to those generated by the control and effectively demonstrate the power of the technique.

Figure 12:
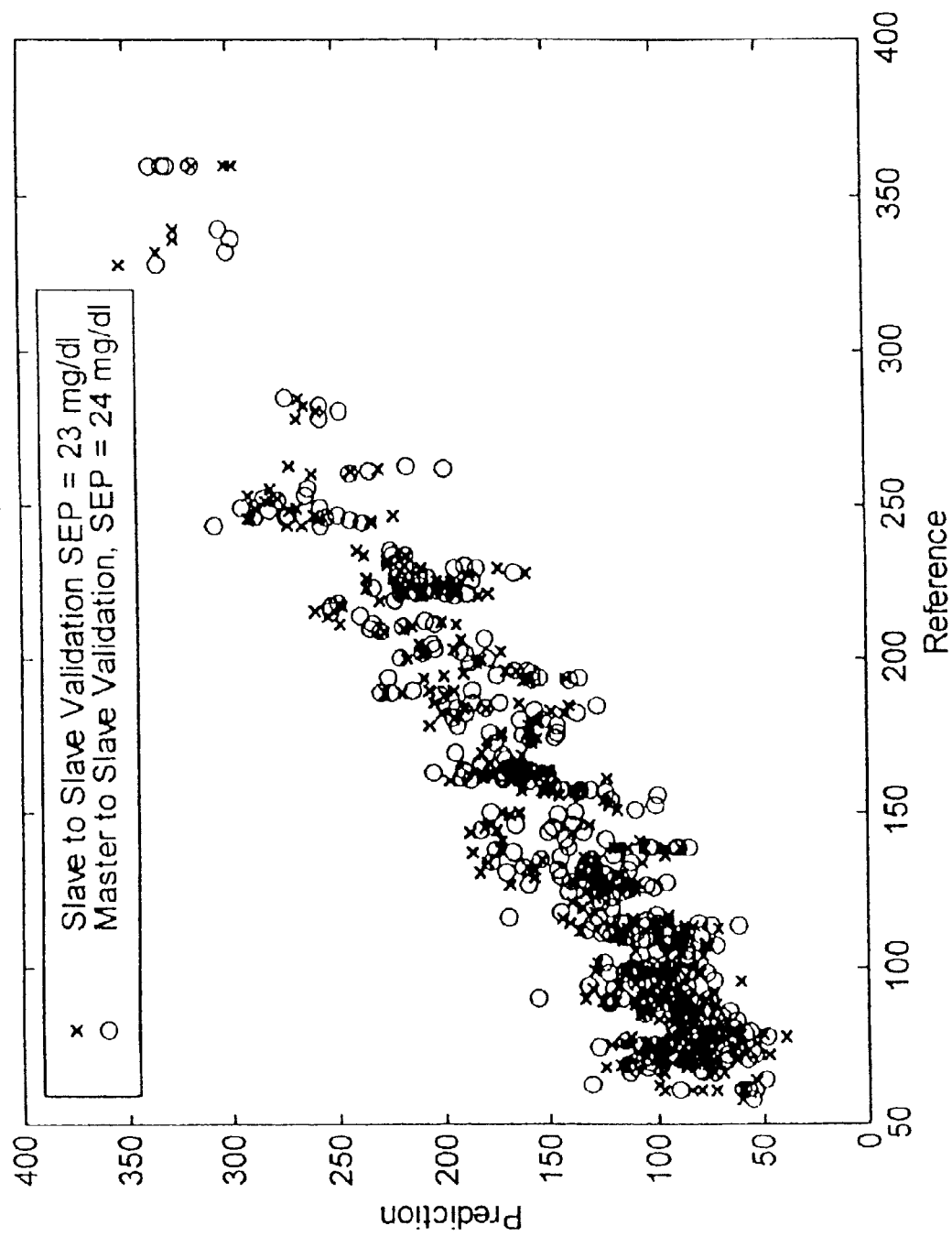
FIG. 12 graphically depicts the ability of the present invention to transfer calibration using composite tailoring.

For the second embodiment, composite tailoring, the data were processed using the composite tailoring method described previously, and shown in FIG. 4. The generic calibration data from a master instrument in combination with an individual subject's tailoring spectra was used to develop the calibration model. The resulting tailored calibration model was developed using partial least squares regression and is specific for both the instrument and subject. The resulting instrument and subject specific model was used to predict on the subject's validation data. The process was repeated for all 11 patients individually. The results for the composite tailoring method for a single instrument are shown in FIG. 12. Again, the prediction results are quite similar to those generated by the control and effectively demonstrate the power of the technique.

As discussed herein, it is also possible to use multiple instruments to create a calibration and transfer this calibration to another instrument not used to create the calibration. FIG. 13 shows the results when the first embodiment (direct tailoring) is used to construct a calibration from two (master) instruments and predict on spectral data collected from a third (slave) instrument. FIG. 14 shows the results when the second embodiment (composite tailoring) is used to construct a calibration from two (master) instruments and predict on data collected from a third (slave) instrument.

The examples discussed above are cited merely to illustrate particular embodiments of this invention. It is contemplated that the use of the invention can involve methods for multivariate calibration and prediction and their application to the non-invasive or non-destructive spectroscopic measurement of selected variables in an environment. Although blood glucose (the variable) and instrument (the environment) are the focus of this disclosure, calibration of other variables such as blood alcohol levels, and other instruments, such as scans of a physical scene from which information about the scene is determined, is contemplated. For example, an airborne scan of a site (geophysical environment) might provide information whereby multivariate analysis of spectra could determine the amount of pollutants (the variables) at the site (the environment), if the scanning device has been calibrated for pollutants. In this case, prediction of pollutant levels would be tailored to a particular site. In another example, one might be interested in predicting the level of a certain chemical species (the variable) in a chemical reactor (the environment) using spectral methods. If the intra-reactor spectral variability were consistent across different reactors, then generic calibration data could be obtained by using reactor-specific subtrahends. Predictions could be tailored to each reactor.

New characteristics and advantages of the invention covered by this document have been set forth in the foregoing description. It will be understood, however, that this disclosure is, in many respects, only illustrative. Changes can be made in details, particularly in matters of shape, size, and arrangement of parts, without exceeding the scope of the invention. The scope of the invention is, of course, defined in the language in which the appended claims are expressed.

We claim:

1. A non-invasive method for determining the presence, concentration, or both of an analyte in tissue of a specific subject comprising the steps of:
    a) providing an apparatus for measuring infrared absorption, said apparatus including an energy source emitting infrared energy at multiple wavelengths, an input element, an output element and a spectrum analyzer;
    b) providing an apparatus for making a direct measurement of the presence, concentration or both of the analyte;
    c) coupling said input and output elements to said tissue;
    d) irradiating said tissue through said input element with multiple wavelengths of infrared energy with resulting absorption of at least some of said wavelengths;
    e) collecting at least a portion of the non-absorbed infrared energy with said output element followed by determining the intensities of said infrared energy; and
    f) determining the presence, concentration, or both of the analyte in the tissue of said specific subject utilizing a multivariate calibration model, based on reference measurements from multiple subjects and one or more reference measurements from said specific subject, wherein each of said reference measurements includes infrared spectroscopic and corresponding direct measurement of a presence, concentration, or both of the analyte.

2. The method of claim 1, wherein the analyte comprises glucose.

3. The method of claim 1, wherein the analyte comprises a glycosolation byproduct.

4. The method of claim 1, wherein the analyte comprises glucose, and wherein the apparatus for making a direct measurement of the concentration comprises an invasive glucose concentration meter.

5. The method of any of claims 1–4, wherein infrared absorption is near infrared absorption.

6. A method as in claim 1, wherein the multivariate calibration model comprises a partial least squares regression on the reference measurements from multiple subjects and one or more reference measurements from the specific subject.

7. The method of claim 1, wherein the multivariate calibration model comprises a partial least squares regression on the reference measurements from multiple subjects, subsequently modified by the one or more reference measurements from the specific subject.

8. The method of claim 7, wherein modifying the multivariate calibration model comprises applying a partial least squares regression to the multivariate calibration model and the one or more reference measurements from the specific subject.

9. A non-invasive method of determining the presence, concentration, or both of an analyte in a subject, comprising:
    a) generating a multivariate calibration model from reference measurements of a plurality of subjects, where the reference measurements are indirect optical spectroscopic measurements and corresponding direct measurements of the presence, concentration, or both of the analyte;

b) collecting tailoring information, where tailoring information comprises reference optical spectroscopic information and corresponding direct measurement pertaining to the subject;

c) collecting sample optical spectroscopic information pertaining to the subject at a different time than the collection of the tailoring information; and d) determining the presence, concentration, or both of the analyte from a combination of the sample optical spectroscopic information, the model, and the tailoring information.

10. The method of claim 9, wherein step d) comprises:

a) determining a relationship between the sample optical spectroscopic information and the tailoring optical spectroscopic information, and b) determining the presence, concentration, or both of the analyte relative to the tailoring direct measurement from the determined relationship and the model.

11. The method of claim 9, wherein step d) comprises:

a) determining a relationship between a combination of the model and the sample optical spectroscopic information, and a combination of the model and the tailoring optical spectroscopic information, and b) determining the presence, concentration, or both of the analyte relative to the tailoring direct measurement from the determined relationship.

12. The method of claim 9, wherein the analyte is glucose or a related compound.

13. The method of claim 12, wherein the optical spectroscopic information is near infrared spectroscopic information.

14. A method as in claim 9, wherein the multivariate calibration model comprises a partial least squares regression on optical spectroscopic information and corresponding reference measurements of a plurality of subjects.

15. The method of claim 9, wherein step d) comprises modifying the multivariate calibration model with the tailoring information, and applying the modified model to the spectroscopic information collected at the first time.

16. The method of claim 15, wherein modifying the multivariate calibration model comprises applying a partial least squares regression to the multivariate calibration model and the tailoring information.

17. A method of determining a presence, concentration, or both of an analyte in a subject, comprising:

a) at a first time, collecting infrared spectroscopic information pertaining to the subject;

b) determining the presence, concentration, or both of the analyte from: (i) the infrared spectroscopic information collected at the first time; (ii) a multivariate calibration model determined from infrared spectroscopic information collected from a plurality of subjects and corresponding direct measurements indicative of the presence, concentration, or both of the analyte for the plurality of subjects; and (iii) tailoring information, where tailoring information comprises infrared spectroscopic information collected from the subject at a second time, different from the first time, and a corresponding direct measurement indicative of the presence, concentration, or both of the analyte in the subject at the second time.

18. The method of claim 17, wherein step b) comprises:

c) determining a relationship between the infrared spectroscopic information pertaining to the subject collected at the first time and the tailoring information; and d) determining the presence, concentration, or both of the analyte relative to the tailoring direct measurement from the relationship determined in step c) and the model.

19. The method of claim 17, wherein step b) comprises:

c) determining a relationship between a combination of the model and the spectroscopic information collected at the first time, and a combination of the model and the tailoring spectroscopic information; and d) determining the presence, concentration, or both of the analyte relative to the tailoring direct measurement from the determined relationship determined in step c).

20. The method of claim 17, wherein the analyte is glucose or a related compound.

21. The method of claim 20, wherein the optical spectroscopic information is near infrared spectroscopic information.

22. A method as in claim 17, wherein the multivariate calibration model comprises a partial least squares regression on the infrared spectroscopic information collected from a plurality of subjects and corresponding direct measurements indicative of the presence, concentration, or both of the analyte.

23. The method of claim 17, wherein step b) comprises modifying the multivariate calibration model with the tailoring information, and applying the modified model to the spectroscopic information collected at the first time.

24. The method of claim 23, wherein modifying the multivariate calibration model comprises applying a partial least squares regression to the multivariate calibration model and the tailoring information.

* * * * *

UNITED STATES PATENT AND TRADEMARK OFFICE
CERTIFICATE OF CORRECTION

| | | |
|---|---|---|
| PATENT NO. | : 7,098,037 B2 | Page 1 of 1 |
| APPLICATION NO. | : 10/222721 | |
| DATED | : August 29, 2006 | |
| INVENTOR(S) | : Michael J. Haass, Robert K. Rowe and Edward V. Thomas | |

It is certified that error appears in the above-identified patent and that said Letters Patent is hereby corrected as shown below:

On the title page item (12), change "Haas et al." to --Haass et al.--

On the title page item (75), change "Michael J. Haas" to --Michael J. Haass--

Before the heading "Technical Field" on column 1 line 24 of the patent, insert the following:

Government Rights
The United States Government has rights in this invention pursuant to Contract No. DE-AC04-94AL85000 between the United States Department of Energy and Lockheed Martin Corporation for the management and operation of Sandia National Laboratory and pursuant to a cooperative research arrangement between Rio Grande Medical Technologies, Inc. and Sandia Corporaton.

Signed and Sealed this

Twelfth Day of December, 2006

JON W. DUDAS
*Director of the United States Patent and Trademark Office*